United States Patent [19]
Sugiyama et al.

[11] Patent Number: 6,080,556
[45] Date of Patent: *Jun. 27, 2000

[54] HELICOBACTER CATALASE NUCLEOTIDE SEQUENCES, THEIR PRODUCTION AND USE

[75] Inventors: Tosiro Sugiyama, Hokkaido; Tomohisa Kawabata; Kazunari Hirayasu, both of Osaka; Takumi Tanaka, Hyogo, all of Japan

[73] Assignee: Wako Pure Chemical Industries, Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/657,868

[22] Filed: May 31, 1996

[30] Foreign Application Priority Data

Jun. 2, 1995 [JP] Japan ................ 7-136564
Apr. 5, 1996 [JP] Japan ................ 8-083512

[51] Int. Cl.⁷ .................................... C12P 21/06
[52] U.S. Cl. ........................... 435/69.1; 514/44
[58] Field of Search ................. 435/69.1; 424/92

[56] References Cited

U.S. PATENT DOCUMENTS 5,262,156  11/1993  Alemohammad ............... 424/92
5,360,732  11/1994  Berka et al. .................. 435/192
5,646,025   7/1997  Mayer ......................... 435/192

FOREIGN PATENT DOCUMENTS 9527506  10/1995  WIPO.
9533482  12/1995  WIPO.

OTHER PUBLICATIONS

Bishai, W. R. et al, 1994, May, vol. 176(10), J. of Bacteriology, p2914–2921.
Bukanov, N.O. et al, Feb. 1994, Molecular Biology vol. 11(3) p509–523.
Jiang et al, May 1996, Molecular Microbiology, vol. 20(4), p833–842.
Sugiyama, T. et al, May 19–22, 1996, Gastroenterology, vol. 110(4 suppl), A266, 1996.
Newell, D. G. et al, Basic and Clinical Aspects of *H. pylori* Infect., 1994, p 223–226, N.Y. Springer–Verlag.
Odenbeit, S. et al, J. of Bacteriol., vol. 178(23), 1996, p 6960–6967.
US–CAFC 96–1175, Regents of U. of California vs Eli Lilly and Company, 1997.
Newell, DG et al, Ecol. Health Dis., vol. 4 (Spec. Iss), SIZO, #H3–1, abstract only, 1991.
Hazell, SL et al, J. of Gen. Microbiol., vol. 137, p57–61, 1991.
Westblom, TU et al, Eur. J. Clin. Microbiol. Infect. Disease, June, vol. 11(6), p522–526, 1992.
Jiang, Q et al, Mol. Microbiol, vol. 20(4), p833–842, 1996.
Doig, P et al, Infect & Immun., Oct. 1994, p4526–p4533, vol. 62(10).
Marshall, BJ., J. Gastroent & Hepatol., vol. 6, p121–124, 1991.
Newell, DG, Scand. J. Gastroenterol, vol. 26, Supp 187, p 31–38, 1991.
Warren, J.R & Marshall, B. *Lancet*, i: 1273 (1983).
Rathbone, B.J. *Lancet*, ii: 1217 (1985).

(List continued on next page.)

*Primary Examiner*—James C. Housel
*Assistant Examiner*—Ginny Allen Portner
*Attorney, Agent, or Firm*—David G. Conlin; George W. Neuner; Dike, Bronstein, Roberts & Cushman LLP

[57] ABSTRACT

Disclosed are amino acid sequences of polypeptides reacting with antibodies to *Helicobacter pylori* (HP), DNAs coding therefor, vectors containing said DNAs, transformants containing said vectors, a method for preparing said polypeptides by cultivating said transformants, and anti-HP antibody assaying reagents and HP gene detecting reagents comprising said polypeptides, thereby enabling specific, quantitative inspection of HP.

7 Claims, 6 Drawing Sheets

OTHER PUBLICATIONS

Rathbone, B.J. Serological response to *Helicobacter pylori*. *Eur. J. gastroenterol. Hepatol.*, Supple. 1:S21–S23 (1992).

von Wulffen H, Heesemann J Bulzow GW et al. *J. of Clin. Microbiol.* 24:716–720. (1986).

Goodwin CS, Blincow E, Peterson G et al. *J. Infect. Dis.* 155: 488–494. (1987).

Stacey AR, Hawtin PR, Newell DG. *Eur. J. Clin. Microbiol. Infect. Dis.* 9:732–737 (1990).

Evans Jr. DJ, Evans DG, Grahm DX et al. *Gastroenterology.* 96:1 004–1008 (1989).

Sugiyama, T. et al. *Gastroenterology.* 101(77–83) (1991).

Sugiyama, T. et al. Nippon Shokakibyo Gakkai–shi (*Journal of Japan Gastrointestinal disease Society*) 85:1128 (1988). Not in English No translation.

```
CP2       : MVNKDVKQTTAFGAPVWDDNNVITAGPRGPVLLQSTWFLEKLAAFDRERI    50
CP2-PCR1  : MVNKDVKQTTAFGAPVWDDNNVITAGPRGPVLLQSTWFLEKLAAFDRERI
CP2-PCR2  : MVNKDVKQTTAFGAPVWDDNNVITAGPRGPVLLQSTWFLEKLAAFDRERI

PERVVHAKGSGAYGTFTVTKDITKYTKAKIFSKVGKKTECFFRFSTVAGE    100
            PERVVHAKGSGAYGTFTVTKDITKYTKAKIFSKVGKKTECFFRFSTVAGE
            PERVVHAKGSGAYGTFTVTKDITKYTKAKIFSKVGKKTECFFRFSTVAGE

*
            RGSADAVRDPRGFAMKYYTEEGNWDLVGNNTPVFFIRDAIKFPDFIHTQK    150
            RGSADAVRDPRGFAMKYYTEEGNWDLVGNNTPVFFIRDAIKFPDFIHTQK
            RGSADAVRDPRGFAMKYYTEEGNWDLVGNDTPVFFIRDAIKFPDFIHTQK

*
            RDPQTNLPNHDMVWDFWSNVPESLYQVTWVMSDRGIPKSFRHMDGFGSHT    200
            RDPQTNLPNHDMVWDFWSNVPESLYQVTWVMSDRGIPKSFRHMDGFGSHT
            RDPQTNLPNPDMVWDFWSNVPESLYQVTWVMSDRGIPKSFRHMDGFGSHT

*              * *        *
            FSLINAKGERFWVKFHFHTMQGVKHLTNEEAAEVRKYDPDSNQRDLFNAI    250
            FSLINAKGERFWVKFHFHTMQGVKHLTNEEAAEVRKYDPDSNQRDLFNAI
            FSLINAKGERFWVKFHFLTMQGVKHLTNEEAAEIRKHDPDSNQRDLFDAI

*                     * *  *
            ARGDFPKWKLSVQVMPEEDAKKYRFHPFDVTKIWYLQDYPLMEVGIVELN    300
            ARGDFPKWKLSVQVMPEEDAKKYRFHPFDVTKIWYLQDYPLMEVGIVELN
            ARGDFPKWKLSIQVMPEEDAKKYRFHPFDVTKIWCLKDYPLTEVGIVELN

*                                *
            KNPENYFAEVEQAAFSPANVVPGIGYSPDRMLQGRLFSYGDTHRYRLGVN    350
            KNPENYFAEVEQAAFSPANVVPGIGYSPDRMLQGRLFSYGDTHCYRLGVN
            KNPENYFAEVEQAAFTPANVVPGIGYSPDRMLQGRLFSYGDTHRYRLGVN

*                                       *
            YPQIPVNKPRCPFHSSSRDGYMQNGYYGSLQNYTPSSLPGYKEDKSARDP    400
            YPQIPVNKPRCPFHSSSRDGYMQNGYYGSLQNYTPSSLPGYKEDKSARDP
            YPQIPVNRPRCPFHSSSRDGYMQNGYYGSLQNYTPSSLPGYKEDKSTRDP

*
            KFNLAHIEKEFEVWNWDYRADDSDYYTQPGDYYRSLPADEKERLHDTIRE    450
            KFNLAHIEKEFEVWNWDYRADDSDYYTQPGDYYRSLPADEKERLHDTIGE
            KFNLAHIEKEFEVWNWDYRADDSDYYTQPGDYYRSLPADEKERLHDTIGE

SLAHVTHKEIVDKQLEHFKKADPKYAEGVKKALEKHQKMMKDMHGKDMHH    500
            SLAHVTHKEIVDKQLEHFKKADPKYAEGVKKALEKHQKMMKDMHGKDMHH
            SLAHVTHKEIVDKQLEHFKKADPKYAEGVKKALEKHQKMMKDMHGKDMHH

*
            TKKKK                                                505
            TKKKK
            MKKKK
```

FIG. 1

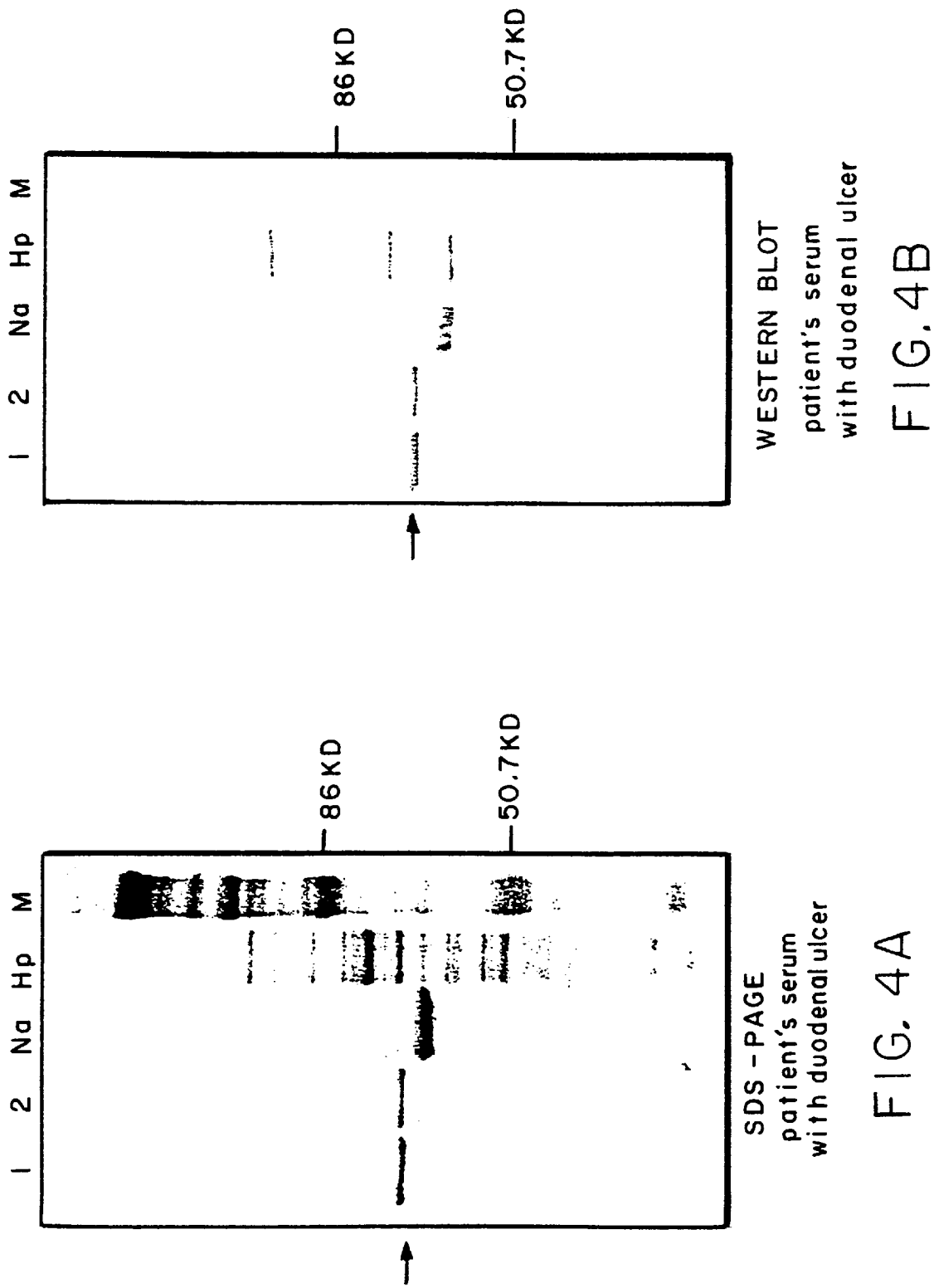

WESTERN BLOT
healthy serum

SDS-PAGE
healthy serum

HELICOBACTER CATALASE NUCLEOTIDE SEQUENCES, THEIR PRODUCTION AND USE

This Application claims foreign priority to Japan Application 83512/1996, filed Apr. 8, 1996 and Japanese Application 136564/1995, filed Jun. 2, 1995.

FIELD OF THE INVENTION

The present invention relates to polypeptides, DNAs coding for said polypeptides, recombinant vectors containing said DNAs, host cells transformed with said recombinant vectors, a method for preparing said polypeptides by cultivating said host cells, and use thereof.

BACKGROUND OF THE INVENTION

*Helicobacter pylori* (which has previously been known as *Campylobacter pylori*) is a Gram-negative bacillus discovered from a chronic gastritis biopsy specimen as a spiral bacterium in 1983 [J. R. Warren and B. Marshall, *Lancet, i,* 1273 (1983)].

After the discovery thereof, the significance of this bacterium to chronic gastritis and duodenal ulcer has attracted attention, and investigation thereof has become one of important themes biologically and medically. In particular, elucidation of the mechanisms of cell injuries leading to diseases and developments of new inspection methods have been gained attention.

Methods for detecting *Helicobacter pylori* (hereinafter briefly referred to as HP) include cultivating methods, urease tests, expiratory tests, histological inspections and serological methods. In particular, the serological methods, in which anti-HP antibodies in the sera are detected, are excellent in that they are noninvasive and a large amount of specimens can be treated.

Various anti-HP antibodies are contained in the sera, so that measurement sensitivity and specificity thereof vary depending on the preparation methods and kind of antigens used for antibody measurement. As a result, the clinical significance of assaying the anti-HP antibodies are also various.

For example, detection methods using lysates of all HP cells as antigens for detection of the anti-HP antibodies [B. J. Rathbone, *Lancet, ii,* 1217 (1985)] sometimes cause false positive judgement due to cross reaction antibodies with other Campylobacter, or conversely, false negative judgement caused by interaction between antigens or denaturation in antigen preparation stages.

B. J. Rathbone reports that antigens partially purified with acidic glycine extract from cells are improved in both specificity and sensitivity than lysates of all HP cells [B. J. Rathbone, "Serological Response to *Helicobacter pylori*", *Eur. J. Gastroenterol. Hepatol.,* 4 (Supple. 1), S21–S23 (1992)]. Furthermore, he reports that methods using urease, etc. highly purified by high performance liquid chromatography (HPLC), etc. as antigens for detection have a tendency to enhance specificity, but to reduce sensitivity because of genetic diversity between HP strains.

Further, of antibodies corresponding to various antigen components of HP, antibodies were screened which were important in relation to utility on serum diagnosis and pathology of gastropathy and duodenal diseases. von Wulffen et al. report that IgG and IgA antibodies are useful, and that particularly, antibodies to 110-KD and 22-KD antigens characteristically appear in the pathology of these diseases [H. von Wulffen, J. Heesemann, G. W. Bulzow et al., *J. Clin. Microbiol.,* 24, 716–720 (1986)]. C. S. Goodwin et al. conduct ELISA using acidic glycine extract as an antigen, and report that main antigen molecules are 84 KD, 33 KD, 28 KD and 25 KD, in addition to 64 KD, 62 KD and 57 KD. [C. S. Goodwin, E. Blincow, G. Peterson et al., *J. Infect. Dis.,* 155, 488–494 (1987)]. Hirschl et al. report that a 128-KD antigen is useful. A. R. Stacey, D. G. Newell et al. fractionate respective antigen components by HPLC, and report that antibodies to HP-derived urease are useful on serum diagnosis [A. R. Stacey, P. R. Hawtin and D. G. Newell, *Eur. J. Clin. Microbiol. Infect. Dis.,* 9, 732–737 (1990)]. D. J. Evans et al. establish ELISA using a 600-KD or more high molecular weight cell-associated protein as an antigen [D. J. Evans Jr., D. G. Evans, D. X. Grahm et al., *Gastroenterology,* 96, 1004–1008 (1986)].

On the other hand, T. Sugiyama et al. try to detect anti-HP antibodies in the blood by use of HP-derived antigens purified by monoclonal antibodies. As a result, they report that an antigen named "CP2 antigen" (molecular weight: about 60 KD) is excellent in detection specificity of HP, and that the antibody titer thereof has a high correlation with the pathology of gastritis [T. Sugiyama et al., *Gastroenterology,* 101, 77–83 (1991) and Toshiroh Sugiyama et al., *Nippon Shokakibyo Gakkaisi,* 85, 1128 (1988)].

In order to actually obtain the HP antigens by the conventional methods, it has hitherto been necessary to isolate the antigens directly from HP cells. However, in order to obtain the HP cells, it is necessary to use expensive liquid media containing 10% horse sera under microaerobic conditions and to conduct culture for a long period of time of about 5 days. Further, the content of the target antigens in all the cells is so small that purification by separation is difficult, resulting in difficulty of obtaining purified antigens in amounts as large as industrially available.

Also for the CP2 antigen which is considered to be particularly useful as a specific antigen, its purification by separation has been difficult and complicated.

SUMMARY OF THE INVENTION

It is therefore an object of the present invention to provide amino acid sequences showing the primary structure of HP-derived polypeptides, DNAs coding for said polypeptides, vectors containing said DNAs, and transformants into which said vectors are introduced, considering the necessity of obtaining genes of the HP-derived polypeptides and enabling mass production by genetic engineering techniques, in order to increase the industrial availability of the HP-derived polypeptides utilized as antigens (CP2 antigen) which mainly make possible specific and quantitative inspection of HP.

Another object of the present invention is to provide a method for preparing said polypeptides.

A further object of the present invention is to provide use of said polypeptides.

Other and further objects of this invention will be apparent from the following description.

As a result of intensive investigation for attaining the above-mentioned objects, the present inventors have succeeded in cloning CP2 antigen genes of HP, and determining the primary structure of the polypeptides of the present invention, the CP2 antigens, from their nucleotide sequences, thus competing the present invention.

That is, the present invention provides:

(1) A polypeptide having an amino acid sequence represented by SEQ ID NO: 4, SEQ ID NO: 5 or SEQ ID NO: 6, or a part thereof;

(2) A DNA coding for an amino acid sequence represented by SEQ ID NO: 1, SEQ ID NO: 2 or SEQ ID NO: 3, or a part thereof;

(3) A DNA having a nucleotide sequence represented by SEQ ID NO: 1, SEQ ID NO: 2 or SEQ ID NO: 3, or a part thereof;

(4) A recombinant vector comprising the DNA described in (2) or (3);

(5) A host cell transformed with the recombinant vector described in (4);

(6) A method for producing the polypeptide described in (1) comprising cultivating the host cell described in (5) in a medium and collecting the polypeptide from the resulting culture product;

(7) A reagent for assay of an anti-*Helicobacter pylori* antibody comprising the polypeptide described in (1);

(8) A reagent for detection of a *Helicobacter pylori* gene comprising a DNA described in (2) or (3), or a DNA complementary to said DNA, and has a property of hybridizing to a *Helicobacter pylori* gene;

(9) A reagent for detection of a *Helicobacter pylori* gene by polymerase chain reaction (PCR) method comprising at least two oligonucleotide primers which are selected from the group consisting of the DNAs described in (2) or (3), and complemental DNAs thereof; and

(10) The reagent of (9) wherein the reagent comprising two oligonucleotide primers, and said oligonucleotide primers have the following characteristics:

(i) one primer hybridizing a strand of *Helicobacter pyloli* gene and another primer hybridizing a strand complementary to the strand, and (ii) being capable of giving an extention product by synthesis, and said extention product being capable of serving as a template for synthesis of the extention product of another primer when it is separated from the complement.

BRIEF DESCRIPTION OF THE DRAWINGS

FIG. 1 shows an amino acid sequence (SEQ ID NO: 4) of a CP2 antigen structural gene obtained in Example 1, an amino acid sequence (SEQ ID NO: 5) of a CP2 antigen structural gene obtained in Example 4 (1), and an amino acid sequence (SEQ ID NO: 6) of a CP2 antigen structural gene obtained in Example 4 (2) in comparison with one another, wherein the reference asterisk (*) marks indicate amino acids in which the difference among the three amino acid sequences of the CP2 antigen structural genes are observed;

FIGS. 4A & B shows results of 4(*a*) sodium dodecylsulfatepolyacrylamide gel electrophoresis of a CP2-PCR1 recombinant protein and a CP2-PCR2 recombinant protein obtained in Example 6 and 4(*b*) Western blotting analysis of a CP2-PCR1 recombinant protein or a CP2-PCR2 recombinant protein obtained in Example 6 and a patient serum;

DESCRIPTION OF THE PREFERRED EMBODIMENTS

Figure 2B:
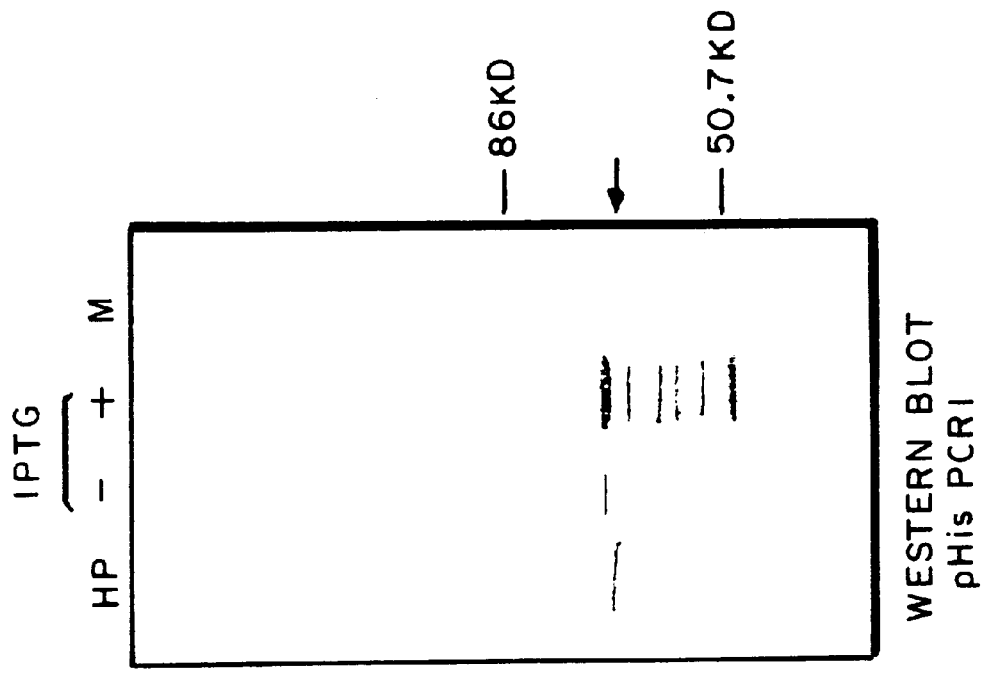
FIGS. 2A & B shows results of 2(*a*) sodium dodecylsulfatepolyacrylamide gel electrophoresis of a CP2-PCR1 recombinant protein obtained in Example 5 and 2(*b*) Western blotting analysis of a CP2-PCR1 recombinant protein obtained in Example 5 and an anti-CP2 monoclonal antibody.

There is no particular limitation on the polypeptide of the present invention, as long as it has an amino acid sequence represented by any of SEQ ID NO: 4, SEQ ID NO: 5 and SEQ ID NO: 6 or a part thereof. More specifically, a polypeptide having the above-mentioned amino acid sequence or a part thereof and having reactivity with an anti-*Helicobacter pylori* antibody is preferred. A so-called modified polypeptide or oligopeptide, a polypeptide or oligopeptide obtained by deleting one or more amino acids from the amino acids constituting the polypeptide or oligopeptide having the amino acid sequence represented by SEQ ID NO: 4, SEQ ID NO: 5 or SEQ ID NO: 6, or having a part thereof; by substituting one or more amino acids thereof by one or more different amino acids; or by inserting one or more different amino acids, is also contained in the category of the polypeptide of the present invention, as long as it has reactivity with an anti-*Helicobacter pylori* antibody.

The DNA of the present invention may be any, as long as it is a DNA which can code for the amino acid sequence represented by any of SEQ ID NO: 4, SEQ ID NO: 5 and SEQ ID NO: 6 or a part thereof. More specifically, a DNA having a nucleotide sequence represented by any of SEQ ID NO: 1, SEQ ID NO: 2 and SEQ ID NO: 3 or a part thereof is preferred.

Namely, such DNAs include a DNA coding for a polypeptide having the amino acid sequence represented by any of SEQ ID NO: 1, SEQ ID NO: 2 and SEQ ID NO: 3 or a part thereof and a polypeptide having a biological activity equivalent thereto.

The DNAs of the present invention may be obtained by any methods. Examples of the DNAs include complementary DNA (cDNA) prepared from mRNA, DNA prepared from genome DNA, DNA obtained by chemical synthesis and DNA constructed by an appropriate combination thereof.

Needless to say, the DNA of the present invention can be substituted by the RNA corresponding thereto in some cases.

The DNA of the present invention coding for the polypeptide for an HP antigen can be obtained by a method of cloning cDNA from mRNA of said polypeptide, a method of isolating from HP genome DNA, a chemical synthesis method or the like.

Examples of the methods of isolating the DNA coding for the HP-derived polypeptide from HP genome DNA include the following methods:

(1) First, HP is cultivated in a liquid medium under microaerobic conditions, and HP cells are separated by centrifugation. The HP cells thus separated are preferably lysed with sodium dodecylsulfate (SDS) and protease K, and then, proteins are denatured by phenol/chloroform extraction to remove them. Thereafter, purified HP genome DNA is prepared [T. J. Slhavy et al., "Experiments with Gene Fusions", pages 137 to 139 (1984)].

The resulting DNA is segmented by partial digestion using an appropriate restriction enzyme or ultrasonication, and the resulting DNA fragment is introduced into an appropriate phage vector, cosmid vector, plasmid vector, etc., thereby constructing a genome DNA library.

There is no particular limitation on the plasmid vector used herein, as long as replication thereof is retained in a host, and the phage vector used may also be any, as long as it can be amplified in a host. However, when subjected to immunological screening methods described later, the vector is required to have a promoter which can express the HP antigen in a host.

Methods for introducing the DNA into the plasmid include, for example, the method described in T. Maniatis et al., *Molecular Cloning, A Laboratory Manual*, 1, 82, Cold Spring Harbor Laboratory, (1982). Methods for introducing the DNA into the phage vector include, for example, the method of T. V. Hyunh et al. [*DNA Cloning, A Practical Approach*, 1, 49 (1985)]. The recombinant plasmid or the phage vector thus obtained is introduced into an appropriate host such as a procaryotic cell and an eucaryotic cell.

Methods for isolating the DNA coding for the HP-derived polypeptide from the DNA library constructed by the above-mentioned method include the following methods.

For example, an oligonucleotide considered to correspond to a partial amino acid sequence of said HP-derived polypeptide is synthesized. Then, the oligonucleotide is labeled with $^{32}$P to prepare a probe, and a clone having the target DNA is selected by the known colony hybridization method [M. Crunstein and D. S. Hogness, *Proc. Natl. Acad. Sci. U.S.A.*, 72, 3961 (1975)] or plaque hybridization method [*Molecular Cloning A Laboratory Manual*, 1, 82, Cold Spring Harbor Laboratory, (1982)]. There are also a method of selecting a clone having the target DNA by use of an antibody (for example, anti-CP2 antibody) to said HP-derived polypeptide utilizing antigen-antibody reaction, and a method of amplifying a specified region of the polypeptide gene by use of the polymerase chain reaction method (PCR method) to isolate the HP-derived polypeptide gene. When the entire region of the gene is not obtained as a result of isolation, the genome DNA library is screened again by colony hybridization or plaque hybridization using the isolated DNA fragment or a part thereof as a probe, whereby the entire gene region can finally be obtained.

The nucleotide sequence of the DNA thus obtained can be determined by the Maxam-Gilbert method [A. M. Maxam and W. Gilbert, *Proc. Natl. Acad. Sci. U.S.A.*, 74, 560 (1977)] or the dideoxynucleotide-chain termination method [J. Messing et al., *Nucleic Acid Res.*, 9, 309 (1981)] to confirm the presence of the HP-derived polypeptide gene. The entire HP-derived polypeptide gene or a part thereof can be obtained by excision with a restriction enzyme from the clone thus obtained.

(2) An oligonucleotide considered to correspond to a partial amino acid sequence of the HP-derived polypeptide is synthesized. Then, the oligonucleotide is labeled with $^{32}$P to prepare a probe, which is hybridized with a digested product of the HP genome DNA prepared in the same manner as with (1) described above with a restriction enzyme such as BamHI, by Southern blotting, thereby preparing a restriction enzyme map in the vicinity of the target gene.

The HP genome DNA thus prepared is digested with an appropriate restriction enzyme to subject the DNA to fragmentation. The DNA fragments are fractionated by molecular weight fractionation such as gel electrophoresis or gel filtration to obtain fractions comprising the target gene-containing DNA fragments with reference to the restriction enzyme map prepared. The group of DNA fragments thus obtained are introduced into plasmid vectors or phage vectors, thereby constructing a restricted HP genome DNA library.

A clone containing the DNA coding for the HP-derived polypeptide is selected by the colony hybridization method or the plaque hybridization method using the above-mentioned probe labeled with $P^{32}$. There are also a method of selecting a clone having the target DNA by use of an antibody (for example, anti-CP2 antibody) to said polypeptide utilizing antigen-antibody reaction, and a method of amplifying a specified region of the polypeptide gene by use of the polymerase chain reaction method (PCR method) to isolate said polypeptide gene. When the entire region of said polypeptide gene isolated is not obtained, the HP genome DNA library is subjected to Southern blot hybridization as described above, using the isolated DNA fragments or parts thereof as a probe, and the HP genome DNA fragment containing the remainder of the target gene is deduced from a group of DNA fragments obtained by digestion with various other restriction enzymes. Using the group of DNA fragments fractionated and obtained by the above-mentioned method, an HP genome DNA library is constructed again, and a clone containing the target DNA is selected using the isolated DNA fragments or parts thereof as a probe, whereby the entire gene region can finally be obtained. The entire HP-derived polypeptide gene or a part thereof can be obtained by excision with a restriction enzyme from the clone thus obtained.

Further, the present invention provides a recombinant vector containing the DNA coding for the above-mentioned HP-derived polypeptide or oligopeptide.

There is no particular limitation on the recombinant vector of the present invention, as long as it contains the DNA coding for the above-mentioned HP-derived polypeptide or oligopeptide, and is replicable or self proliferated in various hosts of procaryotic cells and/or eucaryotic cells. Such vectors include vectors constructed by the known constructing methods of the recombinant vectors [for example, *Molecular Cloning, A Laboratory Manual*, 1, 82, Cold Spring Harbor Laboratory, (1982), etc.].

There is no particular limitation on a vector used when the recombinant vector of the present invention is constructed, as long as it is replicable or self proliferated in various hosts of procaryotic cells and/or eucaryotic cells such as plasmid vectors and phage vectors. Examples thereof include natural plasmids, artificially modified plasmids (DNA fragments prepared from natural plasmids) and synthetic plasmids.

The recombinant vector of the present invention can also be prepared simply by introducing the DNA coding for the polypeptide or the oligopeptide into a vector available in this industry in the usual way. Examples of such vectors include *Escherichia coli*-derived plasmids such as pBR322, pBR325, pUC12, pUC13 and pBluescript, yeast-derived plasmids such as pSH19 and pSH15, and *Bacillus subtilis*-derived plasmids such as pUB110, pTP5 and pC194. Further, examples of the phage vectors include bacteriophages such as λ phage, and viruses of animals and insects such as retroviruses, vaccinia viruses and nuclear polyhedrosis viruses. Preferably, the vectors include plasmid vectors and bacteriophages.

In order to attain the object of expressing the DNA coding for the HP-derived polypeptide or oligopeptide to produce the protein, it is desirable to introduce said DNA into an expression vector when the recombinant vector of the present invention is constructed.

When the host cell is *E. coli.*, preferred examples of such expression vectors available in this industry include pBR322, pUC12, pUC13, pTrcHis, pMAL-c2, pMAL-p2 and artificially modified vectors (DNA fragments obtained by treating said vectors with restriction enzymes). When the host cell is yeast, preferred examples thereof include plasmids pRS403, pRS404, pRS413, pRS414 and pYES. When the host cell is an animal cell, preferred examples thereof include plasmids pRSVeno ATCC 37224, pSV2dhfr ATCC 37145, pdBPV-MMTneo ATCC 37224 and pSV2neo ATCC 37149. When the host cell is an insect cell, preferred examples thereof include *Autoaraphica californica* nuclear polyhedrosis virus (AcNPV) and *Bombyx mori* nuclear polyhedrosis virus (BmNPV).

When a bacterium, particularly *E. coli* is used as the host cell, the recombinant vector of the present invention generally contains a promoter-operator region, an initiation codon, the DNA of the present invention coding for the HP-derived polypeptide or oligopeptide, a termination codon, a terminator region, etc.

Further, when yeast or an animal cell is used as the host cell, the recombinant vector of the present invention generally contains a promoter, an initiation codon, the DNA coding for the HP-derived polypeptide or oligopeptide of the present invention, a termination codon, etc. Into the recombinant vector may be optionally introduced a DNA coding for a signal peptide, an enhancer sequence or a non-translation regions on the 5'- and 3'-terminal sides of the HP-derived polypeptide or oligopeptide.

The promoter-operator region for expressing the HP-derived polypeptide of the present invention in a bacterium includes a promoter, an operator and a Shine-Dalgarno (SD) sequence (for example, AAGG or the like). For example, when the host cell is Escherichia, there is suitably used a Trc (trp-lac) promoter, a Tac promoter, a Trp promoter, a lac promoter, a recA promoter, a λPL promoter or an lpp promoter. The promoters for expressing the polypeptide of the present invention in yeast include a PHO5 promoter, a PGK promoter, a GAP promoter and an ADH promoter. When the host cell is Bacillus, the promoters include an SLO1 promoter, an SPO2 promoter and a penp promoter. Further, when the host cell is an eucaryotic cell such as an animal cell, the promoters include a SV40-derived promoter, a retrovirus promoter and a nuclear polyhedrosis virus promoter. However, the promoters are not limited thereto.

For expression, a method in which isopropyl-β-D-thiogalactoside is added to induce expression, or use of an enhancer is an effective method.

Preferred examples of the initiation codons include a methionine codon (ATG).

Examples of the termination codons include termination codons of common use (for example, TAG and TGA).

The terminator regions include natural and synthetic terminators. Examples of the enhancer sequences include the sequence of SV40 (72 bp), DNA oncogenic viruses such as polyoma, adeno and papilloma viruses, retrovirus long term repeat (LTR), immunoglobulin H chain and L chain genes. The expression vector can be prepared by binding the promotor, the initiation codon, the DNA coding for the HP-derived polypeptide of the present invention, the termination codon and the terminator region successively and cyclically to an appropriate replicable unit. In this case, an appropriate DNA fragment (for example, a linker) can be optionally used according to conventional methods such as digestion with a restriction enzyme and ligation using T4 DNA ligase.

The transformant of the present invention (hereinafter used as the concept including a transductant) can be prepared by introducing the above-mentioned expression vector into a host cell.

Examples of the host cells include microorganisms such as bacteria (for example, Escherichia and Bacillus), yeast (for example, Saccharomyces), animal cells and insect cells. Specifically, examples of the Escherichia include *E. coli* such as DH1, M103, JA221, HB101, C600, XL-1, Blue, JM109 and TOP10. Examples of the Bacillus include *Bacillus subtilis* such as MI114 and 207–21. Examples of the yeast include *Saccharomyces cerevisiae* such as AH22, AH22R⁻, NA87-11A and DKD-5D. The animal cells include monkey cell COS-7, Vero, Chinese hamster cell CHO, mouse L cell and human L cell. The insect cells include BmN4 and Sf9. However, the host cells are not limited thereto.

For cloning of the DNA sequence and construction of the vector, it is generally preferred to use a procaryotic cell as the host cell. Then, the constructed vector is transformed into an appropriate host cell. In this case, a procaryotic cell and an eucaryotic cell can be used.

Introduction (transformation including transduction) of the vector into the host cell can be conducted by methods known in the art.

The transformation can be conducted, for example, by the method of Cohen et al. [*Proc. Natl. Acad. Sci. U.S.A.*, 69, 2110 (1972)], the protoplast method [*Mol. Gene Genet.*, 168, 111 (1979)] or the competent method [*J. Mol. Biol.*, 56, 209, (1971)] for the bacteria (for example, *E. coli* and *Bacillus subtilis*), and for example, by the method of Hinnen et al. [*Proc. Natl. Acad. Sci. U.S.A.*, 75, 1927 (1978)] or the lithium method [*J. Bacteriol.*, 153, 163 (1983)] for *Saccharomyces cerevisiae*. In the case of the animal cells, the transformation can be performed, for example, by the method of Graham [*Virology*, 52, 456 (1973)]. However, methods for transformation are not limited thereto.

The HP-derived polypeptide of the present invention can be produced by cultivating the transformant containing the expression vector prepared as described above in a nutrient medium.

The nutrient media preferably contain carbon sources, inorganic nitrogen sources or organic nitrogen sources necessary for growth of the host cells (transformants). Examples of the carbon sources include glucose, dextrin, soluble starch and sucrose. Examples of the inorganic or organic nitrogen sources include ammonium salts, nitrates, amino acids, corn steep liquor, peptone, casein, meat extracts, soybean meal and potato extract solution. Further, the media may contain other nutrients such as inorganic salts (for example, calcium chloride, sodium dihydrogenphosphate and magnesium chloride), vitamins and antibiotics (for example, ampicillin and kanamycin) if necessary.

The cultivation is conducted according to methods known in the art. Cultivation conditions such as the temperature, the pH of media and the fermentation time are appropriately selected so as to give the maximum titer as antigens of said polypeptides.

Specific media and cultivation conditions used according to the hosts are shown below, but are not limited thereto.

When the host cell is a bacterium, Actinomyces, yeast or a mold, for example, a liquid medium containing the above-mentioned nutrient(s) is suitably used. In that case, the pH is preferably 5 to 8.

When the host cell is *E. coli,* preferred examples of the media are LB medium, YT medium, SOB medium [*Molecular Cloning, A Laboratory Manual,* 1, 82, Cold Spring Harbor Laboratory, (1982)] and M9 medium [Miller, *J. Exp. Mol. Genet.,* page 431, Cold Spring Harbor Laboratory, New York (1972)]. In such cases, the cultivation can be carried out usually at 14 to 42° C., preferably at 28 to 39° C., for about 3 to 24 hours with aeration or agitation if necessary.

When the host cell is Bacillus, the cultivation can be carried out usually at 14 to 42° C., preferably at 28 to 39° C., for about 3 to 96 hours with aeration or agitation if necessary.

When the host cell is yeast, examples of the media include the medium developed by K. L. Bostian et al. [K. L. Bostian et al., *Proc. Natl. Acad. Sci. U.S.A.,* 77, 4505 (1980)], which preferably has a pH of 5 to 8. The cultivation can be carried out usually at 14 to 42° C., preferably at 20 to 35° C., for about 12 hours to 10 days with aeration or agitation if necessary.

When the host cell is an animal cell, examples of the media which can be used include MEM medium containing about 5 to 20% fetal calf serum [*Science,* 122, 501 (1952)], DMEM medium [*Virology,* 8, 396 (1959)], RPMI 1640 medium [*J. Am. Med. Assoc.,* 199, 519 (1967)] and 199 medium [*Proc. Soc. Biol. Med.,* 73, 1 (1950)]. The pH of the media is preferably about 6 to 8, and the cultivation is carried out usually at about 30 to 40° C., preferably at 34 to 38° C., for about 12 to 72 hours with aeration or agitation if necessary.

When the host cell is an insect cell, examples of the media include Grace's insect medium [*Proc. Natl. Acad. Sci. U.S.A.,* 82, 8404 (1985)] supplemented with fetal calf serum. The pH of the medium is preferably adjusted to about 5 to 8. The cultivation is carried out usually at about 20 to 40° C., preferably at 25 to 30° C. for about 12 hours to 10 days with aeration or agitation if necessary.

The HP-derived polypeptides of the present invention can be obtained according to the following methods from culture products obtained by the above-mentioned cultivation.

That is, when the HP-derived polypeptides of the present invention exist in culture solutions of the culture products, the resulting culture products are subjected to filtration or centrifugation to obtain culture filtrates (supernatants). Then, the polypeptides are isolated and purified from the culture filtrates by conventional methods generally used for isolation and purification of natural or synthetic proteins.

The isolating and purifying methods include methods utilizing a difference in solubility such as salting-out and solvent precipitation, methods utilizing a difference in molecular weight such as dialysis, ultrafiltration, gel filtration and sodium dodecylsulfonate-polyacrylamide gel electrophoresis (SDS-PAGE), methods utilizing specific affinity such as affinity chromatography, methods utilizing a difference in hydrophobicity such as reverse phase high performance liquid chromatography, and methods utilizing a difference in isoelectric point such as isoelectric point electrophoresis.

On the other hand, the HP-derived polypeptides of the present invention exist in periplasms or cytoplasms of the cultivated transformants, culture products are subjected to conventional methods such as centrifugation to collect cells, thereafter the cells are suspended in appropriate buffer solutions. Then, cell walls and/or cell membranes are disrupted, for example, by ultrasonication, lysozyme, freeze-thawing or the like, followed by centrifugation or filtration to obtain crude fractions containing the polypeptides. Thereafter, said crude fractions can be isolated and purified according to the conventional methods shown above.

The polypeptides of the present invention can be used as antigens in immunoassays such as enzyme immunoassay (EIA), radio immunoassay (RIA) and fluorescent immunoassay (FIA), thereby detecting anti-HP antibodies in samples.

More specifically, for example, the polypeptide fixed on an appropriate carrier is first reacted with a sample to form a polypeptide-anti-HP antibody complex, and a labeled anti-human immunoglobulin antibody is reacted therewith. Thereafter, the anti-HP antibody is assayed on the basis of the label. According to another embodiment, the polypeptide is labeled, and then, the labeled polypeptide is reacted with a sample. After normal B/F separation, the anti-HP antibody is assayed using the label. The polypeptides used in the immunoassays may be either parts of the polypeptides or peptide chains of parts of the polypeptides obtained by chemical synthesis, etc., as long as they can be used as antigens to the anti-HP antibodies. They may also be polypeptides such as fused proteins containing the polypeptides, parts of the polypeptides or the peptide chains.

Thus, these peptides can be used as anti-HP antibody assaying reagents. For example, enzyme immunoassay can be conducted using an anti-HP antibody assaying kit comprising a carrier such as a microplate or beads on which the polypeptide, part of the polypeptide, the peptide chain or the polypeptide containing them as described above is fixed, an enzyme-labeled anti-human immunoglobulin antibody and a substrate exhibiting color development, luminescence or fluorescence, whereby HP in a sample can be detected specifically and highly sensitively.

Further, these peptides have reactivity with anti-Hp antibodies which means that these peptides have an epitope recognized by the anti-Hp antibodies. Therefore, these peptides have productivity of an anti-Hp antibody which enhances an immnoability specific to Hp. Accordingly, the peptides of the present invention can be used as vaccine against HP which prevents an infection of HP or a crisis thereof.

Further, when an oligonucleotide primer for PCR method is appropriately prepared based on the nucleotide sequence of the DNA of the present invention or the DNA complementary thereto, HP in a sample can also be detected specifically and highly sensitively by the PCR method, for example, using the gastric juice, or the pathologic tissue of the stomach or the duodenum as the sample. Similarly, an oligonucleotide or a polynucleotide is appropriately prepared based on the nucleotide sequence of the DNA of the present invention or the DNA complementary thereto, and hybridization is conducted utilizing this as a labeled probe, whereby HP in a sample can also be detected specifically and highly sensitively.

Thus, these DNAs can be used as HP detecting reagents. For example, the PCR method, LCR (ligase chain reaction) method and the like using an HP gene detecting kit comprising an oligonucleotide primer appropriately selected as described above, a thermostable DNA polymerase and dNTP (DATP, dCTP, dGTP or dTTP), a substrate thereof, can detect HP in a sample specifically and highly sensitively. The known PCR methods include PCR-SSCP (PCR single-strand conformation polymorphism) method, RT-PCR (reverse transcription PCR) method, LA-PCR (long and accurate PCR) method, inverse-PCR method, SSP-PCR (single specific PCR) method and the like [See, BIO MANUAL UP SERIES, "PCR ho no saishingijutsu (new techniques of PCR method)" edited by Takeshi HAYASHI, the first version: Feb. 5, 1995, the second version: Oct. 25, 1995, Yohdosha]. Regarding LCR method, see GENDAI YOGO HYAKKA, Biotechnology, Tohru MARUNOUCHI et al., Jun. 1, 1994, Tokyo Kagaku Dohjin. A reagent for PCR method using the oligonucleotide primers is preferable to contain two oligonucleotide primers, and said oligonucleotide primers to have the following characteristics:

(i) one of the primers hybridyzing a strand of *Helicobacter pyloli* gene and other primer hybridyzing a strand complementary to the strand, and (ii) being capable of giving an extention product by synthesis, and the extention product being capable of serving as a template for synthesis of the extention product of other primer when it is separated from the complement.

The oligonucleotide primers for the PCR methods include the following sets of a forward primer and a reverse primer. The oligonucleotide primers which show homology between several HP cell lines such as the following sets are especially effective for a detection of a HP gene.

forward primer: GCCCTAGAGGTCCTGTTTTATT
97th to 118th nucleotide sequence of SEQ ID NO:1
80th to 101st nucleotide sequence of SEQ ID NO:2 or NO:3 reverse primer: CCTTCTTCAGTQTAATACTTCA
complementary sequence of 364th to 385th nucleotides of SEQ ID NO:1
complementary sequence of 347th to 368th nucleotides of SEQ ID NO:2 or NO:3 forward primer: GATTCCATCCGTTTGATGTGACT
841st to 863rd nucleotide sequence of SEQ ID NO:1
824th to 846th nucleotide sequence of SEQ ID NO:2 or NO:3 reverse primer: ATCAGCTCTGTAATCCCAATTCC
complementary sequence of 1261st to 1283rd nucleotides of SEQ ID NO:1
complementary sequence of 1244th to 1266th nucleotides of SEQ ID NO:2 or NO:3

Alternatively, for example, the hybridization method using an HP gene detecting kit comprising a polynucleotide probe or an oligonucleotide probe appropriately selected as described above can also detect HP in a sample specifically and highly sensitively. The above-mentioned HP gene includes RNA, as well as DNA.

Plasmids, enzymes such as restriction enzymes and T4 ligase and other materials used in the following examples are commercially available ones, and used according to conventional methods. Further, cloning of DNAs, transformation of host cells, cultivation of transformants, collection and purification of polypeptide antigens for specific detection of HP from resulting culture products, etc. are conducted by methods known in the art or available in the literature.

The present invention will be described in more detail through the following examples. It is understood of course that they are not intended to limit the scope of the invention.

EXAMPLE 1

Determination of Nucleotide Sequence of DNA Coding for CP2 Antigen, and Amino Acid Sequence of CP2 Antigen (1) Determination of N-Terminal Amino Acid Sequence of CP2 Antigen A Brucella agar plate (Difico Laboratories, Detroit, Md.) containing 10% horse blood was seeded with HP (ATCC 43504, Rockville, Md.), and cultivated at 37° C. for 5 days under microaerobic conditions. Then, 450 ml of Brucella medium containing 10% horse blood was seeded with the grown HP colony, and cultivated at 37° C. for 5 days under microaerobic conditions. Cells were recovered by centrifugation (6,000 rpm), and washed with PBS (0.1 M sodium phosphate, pH 7.4, 0.15 M NaCl). The cells were disrupted and solubilized by ultrasonication, and a fraction near about 60 KD of SDS-PAGE (a fraction reacting with an anti-CP2 monoclonal antibody [T. Sugiyama et al., *Gastroenterology*, 101, 77–83 (1991)] was fractionated by use of a Prep Cell (an electrophoresis device for fractionation of proteins, Bio RAD). After this procedure was repeated three times, the fraction was introduced into a Sepharose 4B column to which the CP2 monoclonal antibody was fixed. The protein fraction absorbed by the column was eluted with 0.2 M glycine hydrochloric acid buffer to obtain a purified CP2 antigen fraction. This fraction was further purified by SDS-PAGE using a Prep cell, and the CP2antigen, an single band on electrophoresis, was used for analysis of amino acid sequences.

The above-mentioned purified CP2 antigen was loaded on an automatic protein sequencer (Type 477-A, ABI), and the N-terminal amino acid sequence thereof was examined. The results revealed the following amino acid sequence of 20 amino acids:

Met Val Asn Lys Asp Val Lys Gln Thr Thr Ala Phe Gly Ala Pro Val Trp Asp Asp Asn

This sequence completely agreed with the sequence reported as the N-terminal sequence of catalase of HP, Met Val Asn Lys Asp Val Lys Gln Thr Thr Ala Phe Gly Ala Pro Val [T. U. Westblom et al., *Eur. J. Clin. Microbiol. Infect. Dis.*, 11 (No. 6), 522–526 (1992)].

(2) Preparation of HP Genome DNA

About 2 g (wet weight) of HP cells (ATCC 43504) was washed twice with 10 ml of ice-cooled PBS (0.1 M sodium phosphate, pH 7.4, 0.15 M NaCl) by centrifugation, and then, suspended in 2.5 ml of 50 mM Tris-HCl (pH 8.0). To the resulting suspension, 120 µl of 10% SDS and 0.5 ml of STEP [0.5% SDS, 50 mM Tris-HCl (pH 7.5), 0.4 M EDTA, 1 mg/ml protease K] were added, followed by reaction at 50° C. for 2 hours. After reaction, 2 ml of TE buffer (pH 8.0) was added thereto, and the reaction product was extracted twice with 5 ml of phenol/chloroform to remove proteins. The reaction product was further extracted twice with the same amount of ether, and thereafter, a 2.5-fold excess of ethanol was added thereto, followed by centrifugation to recover a mixture of DNA and RNA as a precipitate. After drying, the precipitate was dissolved in 1 ml of TE buffer, and 200 µg of RNaseA was added thereto. The resulting solution was maintained at 37° C. for 1 hour. The solution was extracted twice with the same amount of phenol/chloroform, and thereafter, further extracted with ether. Then, about 1 mg of purified DNA was obtained by ethanol precipitation.

(3) Cloning of CP2 Antigen Gene

An oligonucleotide (17 nucleotides) synthesized by deduction from the information of the CP2 antigen N-terminal sequence was labeled with $\gamma^{32}$P-ATP to prepare a probe. Digested products of HP genome DNA with various restriction enzymes (PstI, HindIII, StuI, HaeIII, Sau3AI, SacI, XbaI, BamHI, ApaI, ClaI, XhoI, etc.) were subjected to Southern blot hybridization analysis using the probe. The results showed that the target DNA reacting with the probe was converted to a fragment having about 400 nucleotides by digesting HP genome DNA with restriction enzyme Sau3AI.

200 μg of HP genome DNA was digested with Sau3AI at 37° C. for 16 hours. The digested product was subjected to agarose gel electrophoresis, and a gel at a position where the DNA fragment of about 400 nucleotides reacting with the probe was electrophoresed was separated. DNA was eluted from the separated gel by electrophoresis, and purified by phenol/chloroform extraction. The purified DNA was recovered by ethanol precipitation, and the precipitate was washed with 70% ethanol, followed by drying to obtain a group of DNA fragments each having about 400 nucleotides. *E. coli* (JM109) was transformed with pBLuescriptIISK into the BamHI site of which the DNA fragment was inserted, thereby obtaining thousands of colonies of transformants on an agar plate.

The colony on the agar plate was transcribed onto a nitrocellulose membrane, and the membrane was immersed in an alkali denaturation solution (1.5 M NaCl, 0.5 M NaOH) for 5 minutes to conduct lysis and DNA denaturation. Then, the nitrocellulose membrane was immersed in a neutralization solution [1 M Tris-HCl (pH 8.0), 1.5 M NaCl] for 5 minutes, and in 2× SSC (0.3 NaCl, 0.03 M sodium citrate) for 5 minutes. Then, the membrane was heated at 80° C. for 2 hours to fix DNA on the membrane. The membrane was immersed in a hybridization solution [6× SSC, 0.1% SDDS, 20 mM Tris-HCl (pH 8.0), 0.125% sodium caseinate, 2.5 mM EDTA, 100 μg/ml denatured salmon sperm DNA] at 42° C. for 1 hour, and thereafter, the above-mentioned oligonucleotide (17 nucleotides) labeled with $\gamma^{32}$P-ATP was added thereto. After reaction with a gradient of −4° C. per hour from 50° C. to 30° C., reaction was further conducted at 30° C. for 8 hours. The nitrocellulose membrane was taken out of the solution, and washed twice with 2× SSC at room temperature for 15 minutes. Then, the membrane was subjected to autoradiography.

The colony judged positive by autoradiography was purified to obtain plasmid pSKC5 into which a DNA fragment of 440 nucleotides containing the N-terminal gene of the CP2 antigen.

Deducing from these results and the restriction enzyme map obtained from the results of the above-mentioned Southern blot hybridization analysis, The C-terminal gene of the CP2 antigen was considered to be contained in an about 600-bp DNA fragment fragmented with PstI and Sau3AI. Then, in order to obtain the remaining region, cloning experiments were carried out as described below.

200 μg of HP genome DNA was partially digested with HaeIII, and the digested product was subjected to agarose gel electrophoresis to separate a fraction of 3- to 4.5-Kbp DNA fragments reacting with the probe. This fraction was further digested with PstI at 37° C. for 3 hours, and the digested product was subjected to agarose gel electrophoresis to separate an about 1.8-Kbp DNA fragment reacting with the probe. The separated DNA fragment was digested with Sau3AI at 37° C. for 1 hour, and the digested product was cloned in the plasmid vector (pMAL-c2) having the PstI-BamHI restriction sites. As a result, plasmid pMBP26 was obtained into which an about 600-bp DNA fragment containing the C-terminal gene of the CP2 antigen was inserted.

The nucleotide sequence of the CP2 antigen gene contained in pSKC5 and pMBP26 was determined by the dideoxy method using DNA Taq polymerase. Using as primers two kinds of synthetic oligonucleotides AAGATG-GTTAATAAAGATGTG (the 18th to 38th nucleotides of SEQ ID NO:1) and AAAATCAATGCTGTATTGAGC (the complementary sequence of the 1800th to 1820th nucleotides of SEQ ID NO:1) prepared with reference to this sequence, the PCR method (30 cycles of 94° C., 300 seconds; 94° C., 90 seconds; 60° C., 120 seconds; and 72° C., 180 seconds; and 72° C., 120 seconds) was conducted to amplify a fragment containing the CP2 antigen structural gene. Both ends of the resulting amplified fragment were made flush, and phosphate groups were added thereto. Then, the resulting fragment was cloned in a pTrcHis expression vector (Invitrogen) having the EcoRI restriction site made flush to obtain plasmid pTrcCP2 containing the CP2 antigen structural gene.

From plasmid pTrcCP2 thus obtained, the nucleotide sequence of the inserted fragment (CP2 fragment) was determined by the dideoxy method using DNA Taq polymerase.

Analysis of this sequence proved a 1829-bp HP genome DNA sequence (SEQ ID NO: 1) containing the sequence of a 1515-bp CP2 antigen structural gene. This revealed the amino acid sequence of the CP2 antigen (SEQ ID NO: 1) composed of 505 amino acid residues having ATG starting from the 21st nucleotide from the 5'-terminus as a translation initiation sequence.

Homology search was conducted for this sequence by use of EMBL of a genetic gene analysis soft and the data bank of GenBank. As a result, this sequence showed 50% or more homology with rat or human catalase.

EXAMPLE 2

Expression of Recombinant CP2 Antigen Protein

Expression vector pTrcCP2 obtained was transformed into *E. coli* (JM109), and cultivated in LB medium overnight. Then, about 3 ml of LB medium was inoculated with 20 μl of the culture solution, and cultivated until an $OD_{600}$ of 0.6 was reached. Two samples of these culture products were prepared, and IPTG was added to one of them to give a final concentration of 1 mM, followed by further cultivation for 3 hours. After termination of cultivation, the two samples were both centrifuged (5000 rpm, 10 minutes). Then, a twice excess of SDS-PAGE loading buffer [125 mM Tris-HCl (pH 6.8), 4% SDS, 0.2% BPB, 20% glycerol] was added to each of the samples, and each of the mixtures was boiled for 3 minutes, followed by SDS-PAGE. As a result, a recombinant CP2 antigen protein expressed by induction of IPTG could be confirmed.

EXAMPLE 3

Reaction of Recombinant CP2 Antigen Protein and Anti-CP2Monoclonal Antibody [T. Sugiyama et al., *Gastroenterology*, 101, 77–83 (1991))

After termination of SDS-PAGE if Example 2, proteins in the polyacrylamide gel were further transcribed onto a nitrocellulose membrane by use of a semidry blotter (Sartorius). Then, the nitrocellulose membrane was shaken in a blocking solution [1% BSA, 20 mM Tris-HCl (pH 7.5), 150 mM NaCl] for 1 hour, and thereafter, an anti-CP2 monoclonal antibody (mouse-derived) was added, followed by further shaking for 1 hour. The nitrocellulose membrane was taken out of the solution, and washed 3 times with TBST [20 mM Tris-HCl (pH 7.5), 150 mM NaCl, 0.05% Tween 20 (v/v)] for 5 minutes. Then, the membrane was further washed 5 times with TBS [20 mM Tris-HCl (pH 7.5), 150 mM NaCl] for 5 minutes. Subsequently, said nitrocellulose membrane was immersed for 1 hour in an alkali phosphatase-labeled anti-mouse IgG antibody solution diluted with a blocking solution. Then, the membrane was taken out of said solution, washed 3 times with TBST for 5 minutes, and further washed 5 times with TBS for 10 minutes. After washing, said nitrocellulose membrane was color developed in a color-developing solution [0.3 mg/ml nitro blue tetrazolium, 0.15 mg/ml 5-bromo-4-chloro-3-indolil phosphate, 100 mM Tris-HCl (pH 9.5), 100 mM NaCl, 5 mM $MgCl_2$].

As a result, the recombinant CP2 antigen protein was found to react with the anti-CP2 monoclonal antibody.

EXAMPLE 4

Acquisition of CP2 Antigen Gene Having Different Primary Structure (1) Acquisition of CP2 Antigen Gene from HP Cell (ATCC 43504)

Using as primers two kinds of synthetic oligonucleotides AAGATGGTTAATAAAGATGTG (the 18th to 38th nucleotides of SEQ ID NO: 1) and AAAATCAATGCTGTATTGAGC (the complementary sequence of the 1800th to 1820th nucleotides of SEQ ID NO: 1) synthesized based on the HP genome sequence (SEQ ID NO: 1) containing the CP2 antigen structural gene determined in Example 1, the PCR method (30 cycles of 94° C., 300 seconds; 94° C., 90 seconds; 60° C., 120 seconds; and 72° C., 180 seconds; and 72° C., 120 seconds) was conducted to the HP genome DNA prepared from the HP cells (ATCC 43504) in Example 1 (1), thereby amplifying a fragment containing the CP2 antigen structural gene. Both ends of the resulting amplified fragment were made flush, and phosphate groups were added thereto. Then, the resulting fragment was cloned in a pBluescript vector having the SmaI restriction site and a pTrcHis expression vector having the EcoRI restriction site made flush to obtain plasmid pBluePCR1 and plasmid pHisPCR2 each containing the CP2 antigen structural gene.

Deletion mutants having various nucleotide lengths were prepared from the resulting plasmid pBluePCR1 by use of a deletion kit (Nippon Gene), and the nucleotide sequence of the inserted fragment (CP2-PCR1 fragment) was determined by the dideoxy method using an ALFred AutoRead Sequencing kit (Pharmacia).

Analysis of this sequence proved a 1803-bp HP genome sequence (SEQ ID NO: 2) containing the sequence of a 1515-bp CP2 antigen structural gene. This revealed that the CP2antigen structural gene in the CP2-PCR1 fragment was different from the CP2 antigen structural gene obtained in Example 1 in 2 nucleotides in the nucleotide sequence, and in 2 amino acids in the amino acid sequence, to which the nucleotide sequence was translated.

A comparison of the amino acid sequence of the CP2antigen structural gene in the CP2-PCR1 fragment and that of the CP2 antigen structural gene obtained in Example 1 in homology is shown in FIG. 1.

(2) Acquisition of CP2 Antigen Gene from HP Clinical Strain

HP genome DNA was prepared from HP cells collected from the stomach of a patient with chronic gastritis (24 years old, male) in a manner similar to that of Example 1 (2).

Using as primers two kinds of synthetic oligonucleotides identical to those used in (1) described above, the PCR method (30 cycles of 94° C., 300 seconds; 94° C., 90 seconds; 60° C., 120 seconds; and 72° C., 180 seconds; and 72° C., 120 seconds) was conducted to the resulting HP genome DNA, thereby amplifying a fragment containing the CP2 antigen structural gene. Both ends of the resulting amplified fragment were made flush, and phosphate groups were added thereto. Then, the resulting fragment was cloned in a pBluescript vector having the SmaI restriction site to obtain plasmid pBluePCR2 containing the CP2 antigen structural gene. Further, the inserted fragment (CP2-PCR2 fragment) was excised with BamHI and XhoI from the plasmid pBluePCR2 thus obtained, and cloned in a pTrcHis expression vector having the BamHI/XhoI restriction sites to obtain plasmid pHisPCR2 containing the CP2 antigen structural gene.

Similarly to (1) described above, deletion mutants having various nucleotide lengths were prepared from the resulting plasmid pBluePCR2 by use of a deletion kit (Nippon Gene), and the nucleotide sequence of the inserted fragment (CP2-PCR2 fragment) was determined by the dideoxy method using an ALFred AutoRead Sequencing kit (Pharmacia).

Analysis of this sequence proved a 1810-bp HP genome sequence (SEQ ID NO: 3) containing the sequence of a 1515-bp CP2 antigen structural gene. This revealed that the CP2antigen structural gene in the CP2-PCR2 fragment was different from the CP2 antigen structural gene obtained in Example 1 in 63 nucleotides in the nucleotide sequence, and in 15 amino acids in the amino acid sequence, to which the nucleotide sequence was translated.

A comparison of the amino acid sequence of the CP2antigen structural gene in the CP2-PCR2 fragment and that of the CP2 antigen structural gene obtained in Example 1 in homology is shown in FIG. 1.

In FIG. 1, the following abbreviations are used:

G: Glycine
A: Alanine
V: Valine
L: Leucine
I: Isoleucine
S: Serine
T: Threonine
D: Aspartic acid
E: Glutamic acid
N: Asparagine
Q: Glutamine
K: Lysine
R: Arginine
C: Cysteine
M: Methionine
F: Phenylalanine
Y: Tyrosine
W: Tryptophan
H: Histidine
P: Proline The upper row, CP2, the middle row, CP2-PCR1, and the lower row, CP2-PCR2 in FIG. 1 indicate the amino acid sequence of the CP2 antigen structural gene obtained in Example 1, the amino acid sequence of the CP2 antigen structural gene (CP2-PCR1) obtained in Example 4 (1), and the amino acid sequence of the CP2 antigen structural gene (CP2-PCR2) obtained in Example 4 (2), respectively.

Further, the reference asterisk (*) marks indicate amino acids in which the difference among the three amino acid sequences of the CP2 antigen structural genes are observed.

Results shown in FIG. 1 reveal that great variation caused by a difference between strains or slight variation in the same strain occurs in the HP-derived CP2 antigen structural genes, that is, the HP-derived CP2 antigens have some variation types.

Furthermore, these results also agree with the report of T. U. Westblom et al. in terms of the HP mutant showing negative catalase activity [*Eur. J. Clin. Microbiol. Infect. Dis.,* 11 (No. 6), 522–526 (1992)].

EXAMPLE 5
Expression of CP2 Antigen Protein and Reaction Thereof with Anti-CP2 Monoclonal Antibody The two kinds of recombinant vectors pHisPCR1 and pHisPCR2 obtained in Example 4 were each transformed into *E. coli* (TOP10), and cultivated in a manner similar to that of Example 2. After termination of cultivation, the samples were centrifuged in a manner similar to that of Example 2, and each subjected to SDS-PAGE in a manner similar to that of Example 2 to confirm the presence or absence of expression of the recombinant CP2 antigen protein. Further, the reactivity of the recombinant CP2antigen protein with the anti-CP2 monoclonal antibody was confirmed by Western blotting analysis similar to that of Example 3.

Figure 2A:
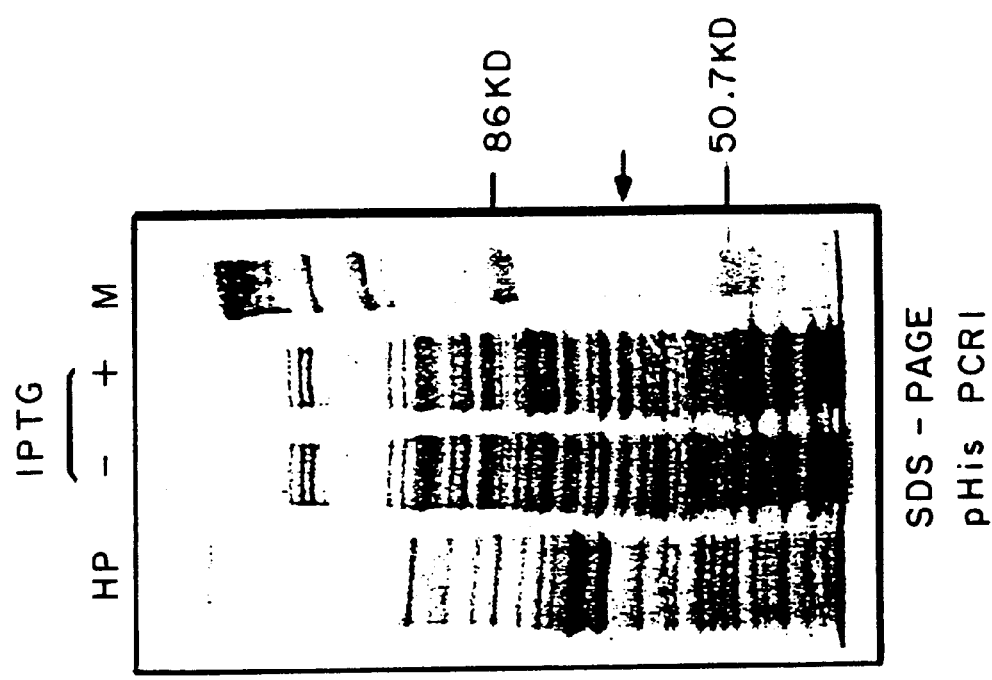

Results of SDS-PAGE of the CP2-PCR1 recombinant protein are shown in FIG. 2(*a*), and results of Western blotting analysis with the anti-CP2 monoclonal antibody using the SDS-PAGE are shown in FIG. 2(*b*).

Figure 3B:
FIGS. 3A & B shows results of 3(*a*) sodium dodecylsulfatepolyacrylamide gel electrophoresis of a CP2-PCR2 recombinant protein obtained in Example 5 and 3(*b*) Western blotting analysis of a CP2-PCR2 recombinant protein obtained in Example 5 and an anti-CP2 monoclonal antibody.
Figure 3A:
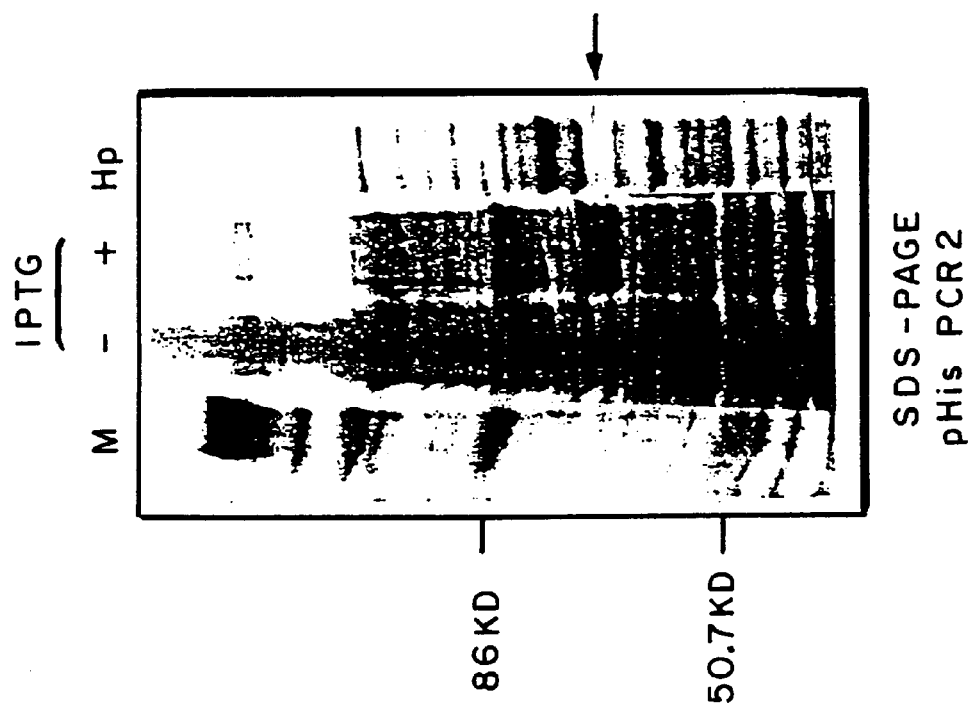

Further, results of SDS-PAGE of the CP2-PCR2 recombinant protein are shown in FIG. 3(*a*), and results of Western blotting analysis with the anti-CP2 monoclonal antibody using the SDS-PAGE are shown in FIG. 3(*b*).

Lane marks in FIGS. 2 and 3 each indicate the results obtained by using the following samples:

Lane M: Molecular weight marker [Prestained SDS-PAGE Standard (Broad Range), Bio RAD]

Hp: HP cell lysate

−: *E. coli* cell lysate before IPTG induction

+: *E. coli* cell lysate after IPTG induction

The arrow (→) marks in FIGS. 2(*a*) and 3(*a*) indicate the positions of the recombinant CP2 antigen proteins, and the arrow (→) marks in FIGS. 2(*b*) and 3(*b*) indicate the positions of reaction signals of the recombinant CP2antigen proteins and the anti-CP2 monoclonal antibody.

Results shown in FIGS. 2(*a*) and 3(*a*) reveal that both the transformants each containing recombinant vectors pHisPCR1 and pHisPCR2 efficiently induce and express about 60-KD recombinant CP2 antigen proteins (CP2-PCR1 and CP2-PCR2 recombinant proteins) by IPTG.

Both the recombinant proteins are expressed as fused proteins each containing 6-mers of histidine residues. They are therefore somewhat larger in molecular weight than the CP2 antigen in the FP-producing protein.

Further, results shown in FIGS. 2(*b*) and 3(*b*) reveal that both the CP2-PCR1 and CP2-PCR2 recombinant proteins have reactivity with the antibody to the HP-derived CP2antigen, namely the anti-CP2 monoclonal antibody.

Furthermore, proteins smaller in molecular weight than the recombinant CP2 antigen proteins (about 60 KD) of the present invention are observed. These proteins are considered to be produced by cleavage of the recombinant CP2 antigen proteins in the host cells. From the finding that these recombinant proteins also have reactivity with the anti-CP2 monoclonal antibody, it is suggested that a partial sequence of the sequence represented by SEQ ID NO: 4, SEQ ID NO: 5 or SEQ ID NO: 6 in the present invention is also available as an antigen for specifically detecting HP.

EXAMPLE 6
Reaction of Recombinant CP2 Antigen Protein and Patient's Serum

The two kinds of recombinant vectors pHisPCR1 and pHisPCR2 obtained in Example 4 were each transformed into *E. coli* (TOP10), and each was cultivated in 50 ml of SOB medium (2% tryptophan, 0.5% yeast extract, 10 mM NaCl, 2.5 mM KCl, 10 mm $MgCl_2$, 10 mM $MgSO_4$) until an $OD_{600}$ of 0.6 was reached. Further, IPTG was added thereto to give a final concentration of 1 mM, and cultivation was conducted for 2 to 5 hours to perform induction and expression due to IPTG. After termination of cultivation, cells were collected by centrifugation (5000 rpm, 10 minutes), and suspended in 10 ml of a lytic buffer [6 M guanidium hydrochloride, 20 mM sodium phosphate, 500 mM sodium chloride]. The resulting suspensions were each subjected to ultrasonication to disrupt the cells, and then, centrifuged (3000 G, 15 minutes) to remove precipitates. The resulting supernatants were each applied to a ProBond resin column (nickel column, Invitrogen) to purify CP2-PCR1 and CP2-PCR2 recombinant CP2 antigen proteins by affinity (the recombinant CP2 antigen proteins are expressed as fused proteins each having 6-mers of histidine residues, so that they show affinity for nickel). Each of the resulting recombinant CP2 antigen proteins was subjected to SDS-PAGE in a manner similar to that of Example 2, and then, the protein in the polyacrylamide gel was transcribed onto a nitrocellulose membrane by use of a semidry blotter (Sartorius). Then, the nitrocellulose membrane was placed in 3 ml of a blocking solution [TBS buffer containing 25% Block Ace (Dainippon Pharmaceutical) and 1% BSA] for 1 hour., 20 mM Tris-HCl (pH 7.5), 150 mM NaCl] at room temperature for 1 hour. Thereafter, 5 μl of the serum of a patient with duodenal ulcer (infected with HP) was added thereto, followed further reaction for 1 hour. After reaction, the nitrocellulose membrane was taken out, washed with TBST buffer, and then, allowed to react in a blocking solution supplemented with an alkali phosphatase-labeled anti-human IgG antibody (Cappel) for 1 hour. As a control, Western blotting analysis was similarly conducted using the serum of a healthy volunteer (normal serum not infected with HP) in place of the patient's serum.

Results of SDS-PAGE of the CP2-PCR1 and CP2-PCR2 recombinant proteins are shown in FIG. 4(*a*), and results of Western blotting analysis with the patient's serum using the SDS-PAGE are shown in FIG. 4(*b*).

Figure 5B:
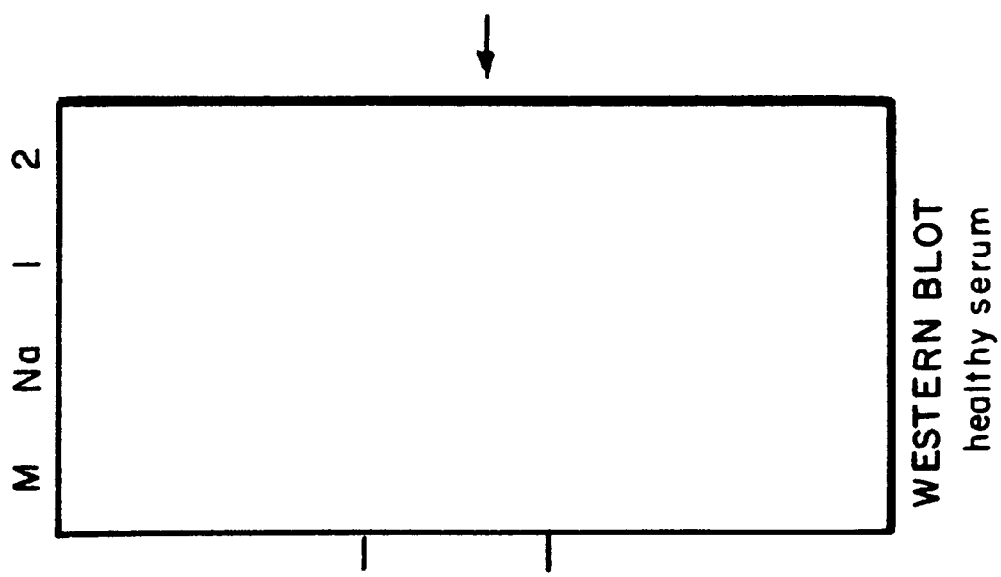
FIGS. 5A & B shows results of 5(*a*) sodium dodecylsulfatepolyacrylamide gel electrophoresis of a CP2-PCR1 recombinant protein and a CP2-PCR2 recombinant protein obtained in Example 6 and 5(*b*) Western blotting analysis of a CP2-PCR1 recombinant protein or a CP2-PCR2 recombinant protein obtained in Example 6 and a healthy human serum.
Figure 5A:

Further, results of SDS-PAGE of the CP2-PCR1 and CP2-PCR2 recombinant proteins are shown in FIG. 5(*a*), and results of Western blotting analysis with the serum of the healthy volunteer using the SDS-PAGE are shown in FIG. 5(*b*).

Lane marks in FIGS. 4 and 5 each indicate the results obtained by using the following samples:

Lane M: Molecular weight marker [Prestained SDS-PAGE Standard (Broad Range), Bio RAD]

Hp: HP cell lysate

Na: CP2 purified from HP cells

1: Purified CP2-PCR1 recombinant protein

2: Purified CP2-PCR2 recombinant protein

The arrow (→) marks in FIGS. 4(*a*) and 5(*a*) indicate the positions of the recombinant CP2 antigen proteins, the arrow (→) marks in FIG. 4(*b*) indicates the position of a reaction signal of the recombinant CP2 antigen protein and the antibody to HP in the serum, and the arrow (→) marks in FIG. 5(*b*) indicates the position where a reaction signal of the recombinant CP2 antigen protein and the antibody to HP in the serum will take place.

Results shown in FIGS. 4(*a*) and 5(*a*) reveal that about 60-KD purified recombinant CP2 antigen proteins (purified CP2-PCR1 and CP2-PCR2 recombinant proteins) are obtained from culture products of the transformants each containing recombinant vectors pHisPCR1 and pHisPCR2, respectively. Both the recombinant proteins are expressed as fused proteins each containing 6-mers of histidine residues.

They are therefore somewhat larger in their molecular weight than the CP2 antigen in the FP-producing protein and the CP2 antigen purified from the HP cells.

Further, results shown in FIG. 4(b) reveal that both the resulting purified recombinant CP2 antigen proteins have reactivity with the anti-CP2 antibody reacting with the CP2 antigen in the FP-producing protein and the CP2antigen purified from the HP cells, namely react with the anti-CP2 antibody in the serum of the patient (infected with HP). Results shown in FIG. 5(b) also reveal that the resulting purified recombinant CP2 antigen proteins do no react with components in the serum of the healthy volunteer.

The above shows that use of the recombinant CP2antigen proteins of the present invention makes it possible to detect the antibodies to HP existing in the sera of the patients, namely to judge from the sera whether they are infected with HP or not, and that the polypeptide useful as antigens for specifically detecting HP are easily obtained in large amounts by cultivating the transformants of the present invention, and separating and purifying the recombinant CP2 antigen proteins from the culture products thereof.

EXAMPLE 7
Evaluation of a Recombinant CP2 antibody by Sandwich ELISA

Each 100 μl of anti-CP2 monoclonal antibody (10 μg/ml) was poured into a 96-hole plate, which was kept overnight at 4° C. to immobilize the antibody. After the immobilization, the plate was washed three times with PBS (10 mM sodium phosphate, 0.15M sodium chloride).

A blocking treatment of the plate was carried out by the following procedures. 400 μl of a blocking solution (PBS, 25% blockAce) was poured into wells of the plate and kept at room temperature for six hours, and then the wells were washed with PBS (three times).

Each 100 μl of a recombinant CP2 antigen (CP2-PCR1, CP2-PCR2 obtained in Example 6) solution (10 μg/ml) was poured into the wells of the above plate, which was kept overnight at 4° C. and then washed with PBS three times.

Each 100 μl of ten samples of patients' serum who are suffered from gastric ulcer, gastric cancer or duodenal ulcer and five samples of serum of healthy volunteers which are diluted 1000 times by the blocking solution was poured into the wells, which was kept overnight at 4° C., and then washed with PBS five times.

Each 100 μl of a coloring solution [10 mg of o-phenylenediamine, 10 μl of 30% hydrogenperoxide aqueous solution and 10 ml of citric phosphate buffer (0.1 M citric acid, 0.2 M disodium hydrogen phosphate, pH 5.0)] was poured into each well, in which the reaction was held at room temperature for 5 minutes to end the reaction with 100 μl of 1N sulphuric acid.

Absorbance of each well was measured by Tmax plate reader manufactured by Molecular-Device Co.) (measure:490 nm, reference:620 nm).

Colors which were caused by anti-Hp antibodies in serum of the healthy volunteers and the patients were determined by Sandwitch ELISA using CP2-PCR1 recombinant protein. The results are shown in Table 1 and FIG. 6(a).

TABLE 1

|  | CP2-PCR1 | CP2-PCR2 |
| --- | --- | --- |
| Patients' serum |  |  |
| gastric cancer | 0.354 | 0.589 |
| gastric cancer | 0.209 | 0.322 |
| gastric ulcer | 0.134 | 0.234 |
| gastric ulcer | 0.215 | 0.278 |
| gastritis | 0.202 | 0.281 |
| gastritis | 0.220 | 0.220 |
| gastric ulcer | 0.217 | 0.223 |
| gastritis | 0.592 | 0.644 |
| duodenal ulcer | 0.269 | 0.389 |
| gastric cancer | 0.202 | 0.283 |
| healthy serum |  |  |
| 1 | 0.047 | 0.083 |
| 2 | 0.033 | 0.041 |
| 3 | 0.060 | 0.068 |
| 4 | 0.101 | 0.128 |
| 5 | 0.049 | 0.064 |

Figure 6B:
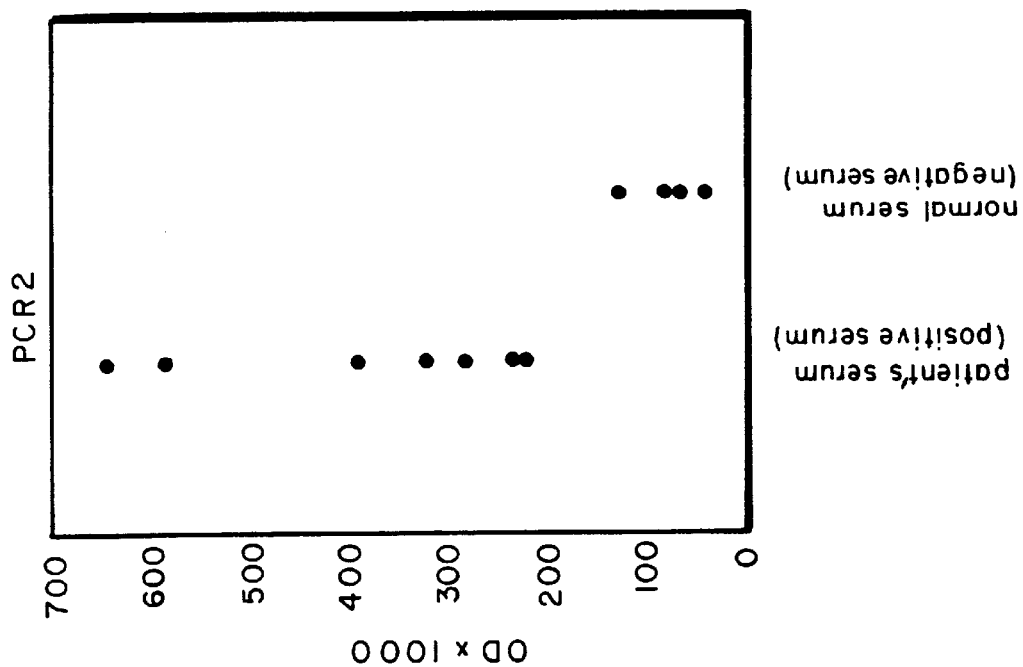
FIGS. 6A & B shows 6(*a*) amounts of color which was caused by an anti-*Helicobacter pylori* (Hp) antibody in serum of healthy volunteers and patients measured by Sandwich ELISA using CP2-PCR1 recombinant protein obtained in Example 7, and 6(*b*) amounts of color which was caused by an anti-*Helicobacter pylori* (Hp) antibody in serum of healthy volunteers and patients measured by Sandwich ELISA using CP2-PCR2 recombinant protein obtained in Example 7.
Figure 6A:
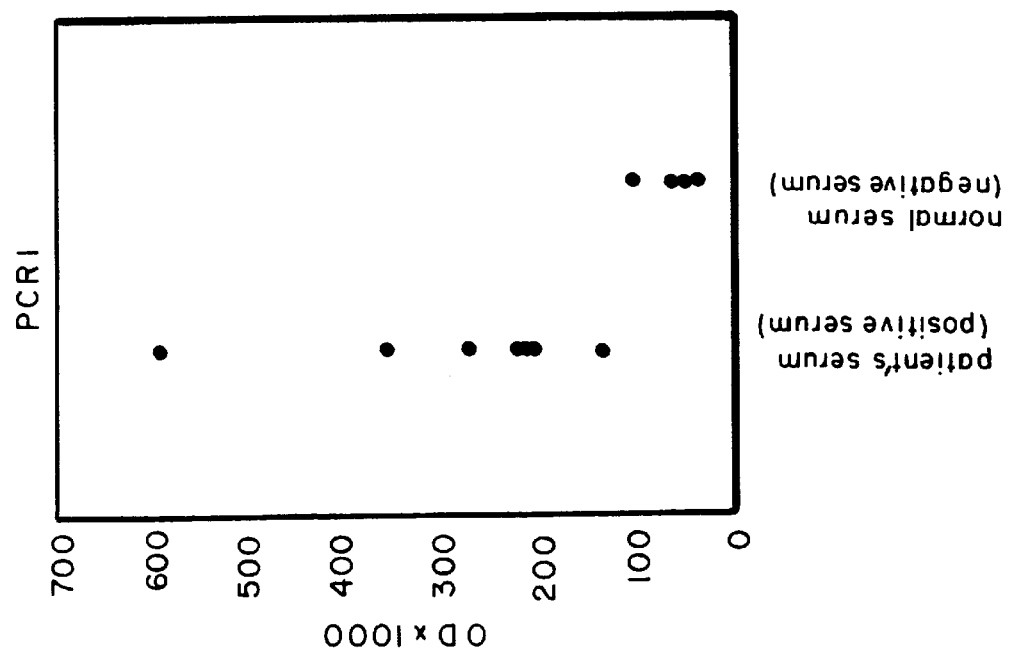

Table 1, FIGS. 6(a) and 6(b) show that measurement of anti-Hp antibodies using recombinant CP2 antigens of the present invention, CP2-PCR1 and CP2-PCR2, give apparent significant difference between patients' serum and healthy serum.

Accordingly, sandwitch ELISA using the recombinant CP2antigens of the present invention detects an anti-Hp antibody with high sensitivity.

The polypeptides of the present invention are utilized as antigens for specifically detecting HP.

Further, use of the DNAs of the present invention allows easy production of the polypeptides available as antigens for specifically detecting HP in large amounts by genetic engineering techniques. Furthermore, preparation of the oligonucleotide primers or the probe by use of DNAs of the present invention also makes it possible to detect HP by the PCR method or the hybridization method.

According to the methods of the present invention, the polypeptide antigens enabling specific detection of HP which has previously been difficult to be achieved can be easily obtained in large amounts.

What is claimed is:

1. An isolated and purified DNA coding for an amino acid sequence represented by SEQ ID NO:4, SEQ ID NO:5 or SEQ ID NO:6.

2. An isolated and purified DNA having a nucleotide sequence represented by SEQ ID NO:1, SEQ ID NO:2 or SEQ ID NO:3.

3. A recombinant vector comprising the DNA as claimed in claim 1 or 2.

4. A host cell transformed with the recombinant vector as claimed in claim 3.

5. A method for producing a polypeptide comprising cultivating the host cell as claimed in claim 4 in a culture medium and collecting the polypeptide from the resulting culture product.

6. An isolated and purified DNA having a nucleotide sequence represented by nucleotides 97–118 of SEQ ID NO:1, nucleotides 364–385 of SEQ ID NO:1, nucleotides 841–863 of SEQ ID NO:1, nucleotides 1261–1283 of SEQ ID NO:1, nucleotides 18–38 of SEQ ID NO:1 and the complementary sequence of nucleotides 1800–1820 of SEQ ID NO:1.

7. A reagent for detection of a Helicobacter gene by a polymerase chain reaction method, said reagent comprising at least two oligonucleotide primers wherein the oligonucleotide primers selected from the group consisting of a DNA having a nucleotide sequence represented by 97–118 of SEQ ID NO:1, nucleotides 364–385 of SEQ ID NO:1, nucleotides 841–863 of SEQ ID NO:1, nucleotides 1261–1283 of SEQ ID NO:1, nucleotides 18–38 of SEQ ID NO:1 and the complementary sequence of nucleotides 1800–1820 of SEQ ID NO:1.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 1829 base pairs
      (B) TYPE: nucleic acid

```
            (C) STRANDEDNESS:  double
            (D) TOPOLOGY:  linear (ii) MOLECULE TYPE:  Genomic DNA (ix) FEATURE:
            (A) NAME/KEY:  Coding Sequence
            (B) LOCATION:  21...1535
            (D) OTHER INFORMATION:

(xi) SEQUENCE DESCRIPTION: SEQ ID NO:1:

GATCAAATAA AGGAAAAAAG ATG GTT AAT AAA GAT GTG AAA CAA ACC ACT          50
                     Met Val Asn Lys Asp Val Lys Gln Thr Thr
                      1               5                  10

GCT TTT GGC GCT CCC GTT TGG GAT GAC AAT GTG ATT ACG GCC GGC           98
Ala Phe Gly Ala Pro Val Trp Asp Asp Asn Val Ile Thr Ala Gly
                15                  20                  25

CCT AGA GGT CCT GTT TTA TTA CAA AGC ACT TGG TTT TTG GAA AAG TTA       146
Pro Arg Gly Pro Val Leu Leu Gln Ser Thr Trp Phe Leu Glu Lys Leu
             30                  35                  40

GCG GCG TTT GAC AGA GAA AGA ATC CCT GAA AGG GTG GTG CAT GCT AAA       194
Ala Ala Phe Asp Arg Glu Arg Ile Pro Glu Arg Val Val His Ala Lys
         45                  50                  55

GGA AGC GGA GCT TAT GGC ACT TTC ACT GTG ACT AAA GAC ATC ACT AAA       242
Gly Ser Gly Ala Tyr Gly Thr Phe Thr Val Thr Lys Asp Ile Thr Lys
     60                  65                  70

TAC ACT AAA GCG AAA ATT TTC TCT AAA GTG GGC AAA AAA ACC GAA TGC       290
Tyr Thr Lys Ala Lys Ile Phe Ser Lys Val Gly Lys Lys Thr Glu Cys
 75                  80                  85                  90

TTC TTC AGA TTT TCC ACT GTG GCT GGT GAA AGA GGC AGT GCG GAT GCG       338
Phe Phe Arg Phe Ser Thr Val Ala Gly Glu Arg Gly Ser Ala Asp Ala
                 95                 100                 105

GTA AGA GAC CCT AGA GGT TTT GCG ATG AAG TAT TAC ACT GAA GAA GGT       386
Val Arg Asp Pro Arg Gly Phe Ala Met Lys Tyr Tyr Thr Glu Glu Gly
            110                 115                 120

AAC TGG GAT TTA GTA GGG AAC AAC ACG CCT GTC TTC TTT ATC CGT GAT       434
Asn Trp Asp Leu Val Gly Asn Asn Thr Pro Val Phe Phe Ile Arg Asp
        125                 130                 135

GCG ATC AAA TTC CCT GAT TTC ATC CAC ACT CAA AAA CGA GAT CCT CAA       482
Ala Ile Lys Phe Pro Asp Phe Ile His Thr Gln Lys Arg Asp Pro Gln
    140                 145                 150

ACC AAT TTG CCT AAC CAT GAC ATG GTA TGG GAT TTT TGG AGT AAT GTT       530
Thr Asn Leu Pro Asn His Asp Met Val Trp Asp Phe Trp Ser Asn Val
155                 160                 165                 170

CCT GAA AGC TTA TAC CAA GTA ACA TGG GTT ATG AGC GAT AGA GGG ATT       578
Pro Glu Ser Leu Tyr Gln Val Thr Trp Val Met Ser Asp Arg Gly Ile
                175                 180                 185

CCT AAA TCT TTC CGC CAC ATG GAT GGT TTT GGC AGT CAC ACT TTC AGT       626
Pro Lys Ser Phe Arg His Met Asp Gly Phe Gly Ser His Thr Phe Ser
            190                 195                 200

CTT ATC AAC GCT AAA GGC GAA CGC TTT TGG GTG AAA TTC CAC TTT CAC       674
Leu Ile Asn Ala Lys Gly Glu Arg Phe Trp Val Lys Phe His Phe His
        205                 210                 215

ACC ATG CAA GGC GTT AAG CAC TTG ACT AAC GAA GAA GCC GCA GAA GTC       722
Thr Met Gln Gly Val Lys His Leu Thr Asn Glu Glu Ala Ala Glu Val
    220                 225                 230

AGA AAA TAT GAT CCT GAT TCC AAT CAA AGG GAT TTA TTC AAT GCG ATC       770
Arg Lys Tyr Asp Pro Asp Ser Asn Gln Arg Asp Leu Phe Asn Ala Ile
235                 240                 245                 250

GCT AGA GGG GAT TTC CCA AAA TGG AAA TTA AGC GTT CAA GTG ATG CCA       818
Ala Arg Gly Asp Phe Pro Lys Trp Lys Leu Ser Val Gln Val Met Pro
                255                 260                 265
```

```
GAA GAA GAT GCT AAG AAG TAT CGA TTC CAT CCG TTT GAT GTG ACT AAA        866
Glu Glu Asp Ala Lys Lys Tyr Arg Phe His Pro Phe Asp Val Thr Lys
            270                 275                 280

ATT TGG TAC CTC CAA GAT TAT CCG TTG ATG GAA GTG GGC ATT GTA GAG        914
Ile Trp Tyr Leu Gln Asp Tyr Pro Leu Met Glu Val Gly Ile Val Glu
        285                 290                 295

TTG AAT AAA AAT CCC GAA AAC TAT TTC GCA GAA GTG GAG CAA GCG GCA        962
Leu Asn Lys Asn Pro Glu Asn Tyr Phe Ala Glu Val Glu Gln Ala Ala
    300                 305                 310

TTC AGT CCG GCT AAT GTC GTT CCT GGA ATT GGC TAT AGC CCT GAT AGG       1010
Phe Ser Pro Ala Asn Val Val Pro Gly Ile Gly Tyr Ser Pro Asp Arg
315                 320                 325                 330

ATG TTA CAA GGG CGC TTG TTC TCT TAT GGG GAT ACA CAC CGC TAC CGC       1058
Met Leu Gln Gly Arg Leu Phe Ser Tyr Gly Asp Thr His Arg Tyr Arg
            335                 340                 345

TTA GGG GTT AAT TAC CCT CAA ATA CCG GTT AAT AAA CCA AGA TGC CCG       1106
Leu Gly Val Asn Tyr Pro Gln Ile Pro Val Asn Lys Pro Arg Cys Pro
        350                 355                 360

TTC CAC TCT TCT AGC AGA GAT GGT TAC ATG CAA AAT GGG TAT TAC GGC       1154
Phe His Ser Ser Ser Arg Asp Gly Tyr Met Gln Asn Gly Tyr Tyr Gly
    365                 370                 375

TCT TTA CAA AAC TAT ACG CCT AGC TCA TTG CCT GGC TAT AAA GAA GAT       1202
Ser Leu Gln Asn Tyr Thr Pro Ser Ser Leu Pro Gly Tyr Lys Glu Asp
380                 385                 390

AAG AGC GCG AGA GAT CCT AAA TTC AAC TTA GCT CAT ATT GAG AAA GAG       1250
Lys Ser Ala Arg Asp Pro Lys Phe Asn Leu Ala His Ile Glu Lys Glu
395                 400                 405                 410

TTT GAA GTG TGG AAT TGG GAT TAC AGA GCT GAT GAT AGC GAT TAC TAC       1298
Phe Glu Val Trp Asn Trp Asp Tyr Arg Ala Asp Asp Ser Asp Tyr Tyr
            415                 420                 425

ACC CAA CCA GGT GAT TAC TAC CGC TCA TTG CCA GCT GAT GAA AAA GAA       1346
Thr Gln Pro Gly Asp Tyr Tyr Arg Ser Leu Pro Ala Asp Glu Lys Glu
        430                 435                 440

AGG TTG CAT GAC ACT ATT AGA GAG TCT TTG GCT CAT GTT ACC CAT AAG       1394
Arg Leu His Asp Thr Ile Arg Glu Ser Leu Ala His Val Thr His Lys
    445                 450                 455

GAA ATT GTG GAT AAA CAA TTG GAG CAT TTC AAG AAA GCT GAC CCC AAA       1442
Glu Ile Val Asp Lys Gln Leu Glu His Phe Lys Lys Ala Asp Pro Lys
460                 465                 470

TAC GCT GAG GGG GTT AAA AAA GCT CTT GAA AAA CAC CAA AAA ATG ATG       1490
Tyr Ala Glu Gly Val Lys Lys Ala Leu Glu Lys His Gln Lys Met Met
475                 480                 485                 490

AAA GAC ATG CAT GGA AAA GAC ATG CAC CAC ACA AAA AAG AAA AAG TAACC    1540
Lys Asp Met His Gly Lys Asp Met His His Thr Lys Lys Lys Lys
            495                 500                 505

CTTTTCTTTA AGCGTTCTTA TTTTTTAGGA ACGCTTTGTC TTTCAAAATT TAGGTTTTTG    1600

GATACTCATC AGTCCTTTGG TGGTGTGTCC TATTTTTTCA TTCATTCAAC GAATTTAAAA    1660

ATTACAATAA AGAGTTATAG TTATGAAACG AAGGGATTTT ATTAAAACGA CTGCTTTAGG    1720

CGCTACAGGT GCTGTTTTAG GAGCACAGAT TTTGCAGGCA GAAGAAAGCA AAGGGAGTGT    1780

TGCAAAATAT AAAATAGAAG CTCAATACAG CATTGATTTT GATTCTGCA               1829
```

(2) INFORMATION FOR SEQ ID NO:2:

(i) SEQUENCE CHARACTERISTICS:
        (A) LENGTH: 1803 base pairs
        (B) TYPE: nucleic acid
        (C) STRANDEDNESS: double
        (D) TOPOLOGY: linear (ii) MOLECULE TYPE: Genomic DNA (ix) FEATURE:
         (A) NAME/KEY: Coding Sequence
         (B) LOCATION: 4...1518
         (D) OTHER INFORMATION:

(xi) SEQUENCE DESCRIPTION: SEQ ID NO:2:

| | | | | | | | | | | | | | | | |
|---|---|---|---|---|---|---|---|---|---|---|---|---|---|---|---|
| AAG | ATG | GTT | AAT | AAA | GAT | GTG | AAA | CAA | ACC | ACT | GCT | TTT | GGC | GCT | CCC | 48 |
| | Met | Val | Asn | Lys | Asp | Val | Lys | Gln | Thr | Thr | Ala | Phe | Gly | Ala | Pro | |
| | 1 | | | 5 | | | | | 10 | | | | | 15 | | |

| GTT | TGG | GAT | GAC | AAC | AAT | GTG | ATT | ACG | GCC | GGC | CCT | AGA | GGT | CCT | GTT | 96 |
| Val | Trp | Asp | Asp | Asn | Asn | Val | Ile | Thr | Ala | Gly | Pro | Arg | Gly | Pro | Val | |
| | | | 20 | | | | | 25 | | | | | 30 | | | |

| TTA | TTA | CAA | AGC | ACT | TGG | TTT | TTG | GAA | AAG | TTA | GCG | GCG | TTT | GAC | AGA | 144 |
| Leu | Leu | Gln | Ser | Thr | Trp | Phe | Leu | Glu | Lys | Leu | Ala | Ala | Phe | Asp | Arg | |
| | | | 35 | | | | 40 | | | | | 45 | | | | |

| GAA | AGA | ATC | CCT | GAA | AGG | GTG | GTG | CAT | GCT | AAA | GGA | AGC | GGA | GCT | TAT | 192 |
| Glu | Arg | Ile | Pro | Glu | Arg | Val | Val | His | Ala | Lys | Gly | Ser | Gly | Ala | Tyr | |
| | | 50 | | | | 55 | | | | | 60 | | | | | |

| GGC | ACT | TTC | ACT | GTG | ACT | AAA | GAC | ATC | ACT | AAA | TAC | ACT | AAA | GCG | AAA | 240 |
| Gly | Thr | Phe | Thr | Val | Thr | Lys | Asp | Ile | Thr | Lys | Tyr | Thr | Lys | Ala | Lys | |
| 65 | | | | | 70 | | | | | 75 | | | | | | |

| ATT | TTC | TCT | AAA | GTG | GGC | AAA | AAA | ACC | GAA | TGC | TTC | TTC | AGA | TTT | TCC | 288 |
| Ile | Phe | Ser | Lys | Val | Gly | Lys | Lys | Thr | Glu | Cys | Phe | Phe | Arg | Phe | Ser | |
| 80 | | | | | 85 | | | | | 90 | | | | | 95 | |

| ACT | GTG | GCT | GGT | GAA | AGA | GGC | AGT | GCG | GAT | GCG | GTA | AGA | GAC | CCT | AGA | 336 |
| Thr | Val | Ala | Gly | Glu | Arg | Gly | Ser | Ala | Asp | Ala | Val | Arg | Asp | Pro | Arg | |
| | | | | 100 | | | | | 105 | | | | | 110 | | |

| GGT | TTT | GCG | ATG | AAG | TAT | TAC | ACT | GAA | GAA | GGT | AAC | TGG | GAT | TTA | GTA | 384 |
| Gly | Phe | Ala | Met | Lys | Tyr | Tyr | Thr | Glu | Glu | Gly | Asn | Trp | Asp | Leu | Val | |
| | | | | 115 | | | | | 120 | | | | | 125 | | |

| GGG | AAC | AAC | ACG | CCT | GTC | TTT | TTT | ATC | CGT | GAT | GCG | ATC | AAA | TTC | CCT | 432 |
| Gly | Asn | Asn | Thr | Pro | Val | Phe | Phe | Ile | Arg | Asp | Ala | Ile | Lys | Phe | Pro | |
| | | | 130 | | | | | 135 | | | | | 140 | | | |

| GAT | TTC | ATC | CAC | ACT | CAA | AAA | CGA | GAT | CCT | CAA | ACC | AAT | TTG | CCT | AAC | 480 |
| Asp | Phe | Ile | His | Thr | Gln | Lys | Arg | Asp | Pro | Gln | Thr | Asn | Leu | Pro | Asn | |
| | 145 | | | | | 150 | | | | | 155 | | | | | |

| CAT | GAC | ATG | GTA | TGG | GAT | TTT | TGG | AGT | AAT | GTT | CCT | GAA | AGC | TTA | TAC | 528 |
| His | Asp | Met | Val | Trp | Asp | Phe | Trp | Ser | Asn | Val | Pro | Glu | Ser | Leu | Tyr | |
| 160 | | | | | 165 | | | | | 170 | | | | | 175 | |

| CAA | GTA | ACA | TGG | GTT | ATG | AGC | GAT | AGA | GGG | ATT | CCT | AAA | TCT | TTC | CGC | 576 |
| Gln | Val | Thr | Trp | Val | Met | Ser | Asp | Arg | Gly | Ile | Pro | Lys | Ser | Phe | Arg | |
| | | | | 180 | | | | | 185 | | | | | 190 | | |

| CAC | ATG | GAT | GGT | TTT | GGC | AGT | CAC | ACT | TTC | AGT | CTT | ATC | AAC | GCT | AAA | 624 |
| His | Met | Asp | Gly | Phe | Gly | Ser | His | Thr | Phe | Ser | Leu | Ile | Asn | Ala | Lys | |
| | | | 195 | | | | | 200 | | | | | 205 | | | |

| GGC | GAA | CGC | TTT | TGG | GTG | AAA | TTC | CAC | TTT | CAC | ACC | ATG | CAA | GGC | GTT | 672 |
| Gly | Glu | Arg | Phe | Trp | Val | Lys | Phe | His | Phe | His | Thr | Met | Gln | Gly | Val | |
| | | | 210 | | | | | 215 | | | | | 220 | | | |

| AAG | CAC | TTG | ACT | AAC | GAA | GAA | GCC | GCA | GAA | GTC | AGA | AAA | TAT | GAT | CCT | 720 |
| Lys | His | Leu | Thr | Asn | Glu | Glu | Ala | Ala | Glu | Val | Arg | Lys | Tyr | Asp | Pro | |
| | 225 | | | | | 230 | | | | | 235 | | | | | |

| GAT | TCC | AAT | CAA | AGG | GAT | TTA | TTC | AAT | GCG | ATC | GCT | AGA | GGG | GAT | TTC | 768 |
| Asp | Ser | Asn | Gln | Arg | Asp | Leu | Phe | Asn | Ala | Ile | Ala | Arg | Gly | Asp | Phe | |
| 240 | | | | | 245 | | | | | 250 | | | | | 255 | |

| CCA | AAA | TGG | AAA | TTA | AGC | GTT | CAA | GTG | ATG | CCA | GAA | GAA | GAT | GCT | AAG | 816 |
| Pro | Lys | Trp | Lys | Leu | Ser | Val | Gln | Val | Met | Pro | Glu | Glu | Asp | Ala | Lys | |
| | | | | 260 | | | | | 265 | | | | | 270 | | |

| AAG | TAT | CGA | TTC | CAT | CCG | TTT | GAT | GTG | ACT | AAA | ATT | TGG | TAC | CTC | CAA | 864 |

```
                    Lys Tyr Arg Phe His Pro Phe Asp Val Thr Lys Ile Trp Tyr Leu Gln
                                275                 280                 285

GAT TAT CCG TTG ATG GAA GTG GGC ATT GTA GAG TTG AAT AAA AAT CCC                 912
Asp Tyr Pro Leu Met Glu Val Gly Ile Val Glu Leu Asn Lys Asn Pro
        290                 295                 300

GAA AAC TAT TTC GCA GAA GTG GAG CAA GCG GCA TTC AGT CCG GCT AAT                 960
Glu Asn Tyr Phe Ala Glu Val Glu Gln Ala Ala Phe Ser Pro Ala Asn
    305                 310                 315

GTC GTT CCT GGA ATT GGC TAT AGC CCT GAT AGG ATG TTA CAA GGG CGC                1008
Val Val Pro Gly Ile Gly Tyr Ser Pro Asp Arg Met Leu Gln Gly Arg
320                 325                 330                 335

TTG TTC TCT TAT GGG GAT ACA CAC TGC TAC CGC TTA GGG GTT AAT TAC                1056
Leu Phe Ser Tyr Gly Asp Thr His Cys Tyr Arg Leu Gly Val Asn Tyr
                340                 345                 350

CCT CAA ATA CCG GTT AAT AAA CCA AGA TGC CCG TTC CAC TCT TCT AGC                1104
Pro Gln Ile Pro Val Asn Lys Pro Arg Cys Pro Phe His Ser Ser Ser
            355                 360                 365

AGA GAT GGT TAC ATG CAA AAT GGG TAT TAC GGC TCT TTA CAA AAC TAT                1152
Arg Asp Gly Tyr Met Gln Asn Gly Tyr Tyr Gly Ser Leu Gln Asn Tyr
        370                 375                 380

ACG CCT AGC TCA TTG CCT GGC TAT AAA GAA GAT AAG AGC GCG AGA GAT                1200
Thr Pro Ser Ser Leu Pro Gly Tyr Lys Glu Asp Lys Ser Ala Arg Asp
    385                 390                 395

CCT AAA TTC AAC TTA GCT CAT ATT GAG AAA GAG TTT GAA GTG TGG AAT                1248
Pro Lys Phe Asn Leu Ala His Ile Glu Lys Glu Phe Glu Val Trp Asn
400                 405                 410                 415

TGG GAT TAC AGA GCT GAT GAT AGC GAT TAC TAC ACC CAA CCA GGT GAT                1296
Trp Asp Tyr Arg Ala Asp Asp Ser Asp Tyr Tyr Thr Gln Pro Gly Asp
                420                 425                 430

TAC TAC CGC TCA TTG CCA GCT GAT GAA AAA GAA AGG TTG CAT GAC ACT                1344
Tyr Tyr Arg Ser Leu Pro Ala Asp Glu Lys Glu Arg Leu His Asp Thr
            435                 440                 445

ATT GGA GAG TCT TTG GCT CAT GTT ACC CAT AAG GAA ATT GTG GAT AAA                1392
Ile Gly Glu Ser Leu Ala His Val Thr His Lys Glu Ile Val Asp Lys
        450                 455                 460

CAA TTG GAG CAT TTC AAG AAA GCT GAC CCC AAA TAC GCT GAG GGG GTT                1440
Gln Leu Glu His Phe Lys Lys Ala Asp Pro Lys Tyr Ala Glu Gly Val
    465                 470                 475

AAA AAA GCT CTT GAA AAA CAC CAA AAA ATG ATG AAA GAC ATG CAT GGA                1488
Lys Lys Ala Leu Glu Lys His Gln Lys Met Met Lys Asp Met His Gly
480                 485                 490                 495

AAA GAC ATG CAC CAC ACA AAA AAG AAA AAG TAACCCTTTT CTTTAAGCGT TCT              1541
Lys Asp Met His His Thr Lys Lys Lys
                500                 505

TATTTTTTAG GAACGCTTTG TCTTTCAAAA TTTAGGTTTT TGGATACTCA TCAGTCCTTT              1601

GGTGGTGTGT CCTATTTTTT CATTCATTCA ACGAATTTAA AAATTACAAT AAAGAGTTAT              1661

AGTTATGAAA CGAAGGGATT TTATTAAAAC GACTGCTTTA GGCGCTACAG GTGCTGTTTT              1721

AGGAGCACAG ATTTTGCAGG CAGAAGAAAG CAAAGGGAGT GTTGCAAAAT ATAAAATAGA              1781

AGCTCAATAC AGCATTGATT TT                                                       1803
```

(2) INFORMATION FOR SEQ ID NO:3:

(i) SEQUENCE CHARACTERISTICS:
        (A) LENGTH: 1810 base pairs
        (B) TYPE: nucleic acid
        (C) STRANDEDNESS: double
        (D) TOPOLOGY: linear (ii) MOLECULE TYPE: Genomic DNA (ix) FEATURE:
    (A) NAME/KEY: Coding Sequence
    (B) LOCATION: 4...1518
    (D) OTHER INFORMATION:

(xi) SEQUENCE DESCRIPTION: SEQ ID NO:3:

| | | | | | | | | | | | | | | | | |
|---|---|---|---|---|---|---|---|---|---|---|---|---|---|---|---|---|
| AAG | ATG | GTT | AAT | AAA | GAT | GTG | AAA | CAA | ACC | ACT | GCT | TTT | GGT | GCT | CCC | 48 |
| | Met | Val | Asn | Lys | Asp | Val | Lys | Gln | Thr | Thr | Ala | Phe | Gly | Ala | Pro | |
| | 1 | | | 5 | | | | | 10 | | | | | 15 | | |
| GTT | TGG | GAT | GAC | AAC | AAT | GTG | ATT | ACG | GCT | GGC | CCT | AGA | GGT | CCT | GTT | 96 |
| Val | Trp | Asp | Asp | Asn | Asn | Val | Ile | Thr | Ala | Gly | Pro | Arg | Gly | Pro | Val | |
| | | | 20 | | | | | 25 | | | | | 30 | | | |
| TTA | TTG | CAA | AGC | ACT | TGG | TTT | TTG | GAA | AAG | TTA | GCA | GCG | TTT | GAT | AGA | 144 |
| Leu | Leu | Gln | Ser | Thr | Trp | Phe | Leu | Glu | Lys | Leu | Ala | Ala | Phe | Asp | Arg | |
| | | | 35 | | | | | 40 | | | | | 45 | | | |
| GAA | AGG | ATT | CCT | GAA | AGG | GTG | GTG | CAT | GCT | AAA | GGA | AGC | GGA | GCT | TAT | 192 |
| Glu | Arg | Ile | Pro | Glu | Arg | Val | Val | His | Ala | Lys | Gly | Ser | Gly | Ala | Tyr | |
| | | 50 | | | | | 55 | | | | | 60 | | | | |
| GGC | ACT | TTC | ACT | GTG | ACT | AAA | GAC | ATC | ACT | AAA | TAC | ACT | AAA | GCG | AAA | 240 |
| Gly | Thr | Phe | Thr | Val | Thr | Lys | Asp | Ile | Thr | Lys | Tyr | Thr | Lys | Ala | Lys | |
| | 65 | | | | | 70 | | | | | 75 | | | | | |
| ATT | TTC | TCT | AAA | GTG | GGC | AAA | AAA | ACC | GAA | TGC | TTT | TTC | AGA | TTT | TCT | 288 |
| Ile | Phe | Ser | Lys | Val | Gly | Lys | Lys | Thr | Glu | Cys | Phe | Phe | Arg | Phe | Ser | |
| 80 | | | | | 85 | | | | | 90 | | | | | 95 | |
| ACT | GTG | GCT | GGC | GAA | AGA | GGC | AGT | GCG | GAT | GCA | GTG | AGA | GAC | CCT | AGA | 336 |
| Thr | Val | Ala | Gly | Glu | Arg | Gly | Ser | Ala | Asp | Ala | Val | Arg | Asp | Pro | Arg | |
| | | | | 100 | | | | | 105 | | | | | 110 | | |
| GGT | TTT | GCG | ATG | AAG | TAT | TAC | ACT | GAA | GAA | GGT | AAT | TGG | GAT | TTA | GTA | 384 |
| Gly | Phe | Ala | Met | Lys | Tyr | Tyr | Thr | Glu | Glu | Gly | Asn | Trp | Asp | Leu | Val | |
| | | | | 115 | | | | | 120 | | | | | 125 | | |
| GGG | AAC | GAC | ACG | CCT | GTT | TTC | TTT | ATC | CGT | GAT | GCG | ATC | AAA | TTC | CCT | 432 |
| Gly | Asn | Asp | Thr | Pro | Val | Phe | Phe | Ile | Arg | Asp | Ala | Ile | Lys | Phe | Pro | |
| | | | 130 | | | | | 135 | | | | | 140 | | | |
| GAT | TTC | ATC | CAC | ACC | CAA | AAA | CGA | GAT | CCT | CAA | ACT | AAT | TTG | CCT | AAC | 480 |
| Asp | Phe | Ile | His | Thr | Gln | Lys | Arg | Asp | Pro | Gln | Thr | Asn | Leu | Pro | Asn | |
| | | 145 | | | | | 150 | | | | | 155 | | | | |
| CCC | GAC | ATG | GTA | TGG | GAT | TTT | TGG | AGT | AAT | GTT | CCT | GAA | AGC | TTG | TAT | 528 |
| Pro | Asp | Met | Val | Trp | Asp | Phe | Trp | Ser | Asn | Val | Pro | Glu | Ser | Leu | Tyr | |
| 160 | | | | | 165 | | | | | 170 | | | | | 175 | |
| CAA | GTA | ACA | TGG | GTT | ATG | AGC | GAT | AGG | GGT | ATT | CCT | AAA | TCT | TTC | CGC | 576 |
| Gln | Val | Thr | Trp | Val | Met | Ser | Asp | Arg | Gly | Ile | Pro | Lys | Ser | Phe | Arg | |
| | | | 180 | | | | | 185 | | | | | 190 | | | |
| CAC | ATG | GAT | GGT | TTT | GGC | AGC | CAC | ACT | TTC | AGC | CTC | ATC | AAC | GCA | AAA | 624 |
| His | Met | Asp | Gly | Phe | Gly | Ser | His | Thr | Phe | Ser | Leu | Ile | Asn | Ala | Lys | |
| | | | 195 | | | | | 200 | | | | | 205 | | | |
| GGC | GAA | CGC | TTT | TGG | GTG | AAA | TTC | CAC | TTT | TTA | ACC | ATG | CAA | GGC | GTT | 672 |
| Gly | Glu | Arg | Phe | Trp | Val | Lys | Phe | His | Phe | Leu | Thr | Met | Gln | Gly | Val | |
| | | | 210 | | | | | 215 | | | | | 220 | | | |
| AAG | CAC | TTG | ACT | AAT | GAA | GAA | GCT | GCA | GAA | ATC | AGA | AAG | CAT | GAT | CCT | 720 |
| Lys | His | Leu | Thr | Asn | Glu | Glu | Ala | Ala | Glu | Ile | Arg | Lys | His | Asp | Pro | |
| | | 225 | | | | | 230 | | | | | 235 | | | | |
| GAT | TCC | AAT | CAA | AGG | GAT | TTA | TTC | GAT | GCG | ATC | GCT | AGA | GGG | GAT | TTC | 768 |
| Asp | Ser | Asn | Gln | Arg | Asp | Leu | Phe | Asp | Ala | Ile | Ala | Arg | Gly | Asp | Phe | |
| 240 | | | | | 245 | | | | | 250 | | | | | 255 | |
| CCA | AAA | TGG | AAA | TTA | AGC | ATT | CAA | GTG | ATG | CCA | GAA | GAA | GAT | GCT | AAG | 816 |
| Pro | Lys | Trp | Lys | Leu | Ser | Ile | Gln | Val | Met | Pro | Glu | Glu | Asp | Ala | Lys | |
| | | | | 260 | | | | | 265 | | | | | 270 | | |
| AAG | TAT | CGA | TTC | CAT | CCG | TTT | GAT | GTG | ACT | AAA | ATT | TGG | TGT | CTC | AAA | 864 |
| Lys | Tyr | Arg | Phe | His | Pro | Phe | Asp | Val | Thr | Lys | Ile | Trp | Cys | Leu | Lys | |
| | | | | 275 | | | | | 280 | | | | | 285 | | |

```
GAT TAT CCA TTG ACG GAA GTG GGC ATT GTA GAG TTG AAT AAA AAT CCT    912
Asp Tyr Pro Leu Thr Glu Val Gly Ile Val Glu Leu Asn Lys Asn Pro
            290                 295                 300

GAA AAC TAT TTC GCA GAA GTG GAA CAA GCG GCA TTC ACT CCG GCT AAT    960
Glu Asn Tyr Phe Ala Glu Val Glu Gln Ala Ala Phe Thr Pro Ala Asn
        305                 310                 315

GTC GTT CCT GGA ATT GGC TAT AGC CCT GAT AGG ATG TTA CAA GGG CGC   1008
Val Val Pro Gly Ile Gly Tyr Ser Pro Asp Arg Met Leu Gln Gly Arg
320                 325                 330                 335

TTG TTC TCT TAT GGG GAC ACA CAC CGC TAC CGC TTA GGG GTT AAT TAT   1056
Leu Phe Ser Tyr Gly Asp Thr His Arg Tyr Arg Leu Gly Val Asn Tyr
            340                 345                 350

CCT CAG ATA CCG GTT AAT AGA CCA AGG TGC CCA TTC CAC TCT TCT AGC   1104
Pro Gln Ile Pro Val Asn Arg Pro Arg Cys Pro Phe His Ser Ser Ser
        355                 360                 365

AGA GAT GGT TAC ATG CAA AAC GGG TAT TAT GGC TCT TTA CAA AAC TAT   1152
Arg Asp Gly Tyr Met Gln Asn Gly Tyr Tyr Gly Ser Leu Gln Asn Tyr
            370                 375                 380

ACG CCT AGC TCA TTG CCA GGT TAT AAA GAA GAT AAG AGC ACG AGA GAT   1200
Thr Pro Ser Ser Leu Pro Gly Tyr Lys Glu Asp Lys Ser Thr Arg Asp
385                 390                 395

CCT AAG TTC AAC TTA GCT CAC ATT GAG AAA GAG TTT GAA GTG TGG AAT   1248
Pro Lys Phe Asn Leu Ala His Ile Glu Lys Glu Phe Glu Val Trp Asn
400                 405                 410                 415

TGG GAT TAC AGA GCT GAT GAT AGC GAT TAC TAC ACC CAA CCA GGT GAT   1296
Trp Asp Tyr Arg Ala Asp Asp Ser Asp Tyr Tyr Thr Gln Pro Gly Asp
            420                 425                 430

TAC TAC CGC TCA TTG CCA GCT GAT GAA AAA GAA AGG TTG CAT GAC ACT   1344
Tyr Tyr Arg Ser Leu Pro Ala Asp Glu Lys Glu Arg Leu His Asp Thr
        435                 440                 445

ATT GGA GAG TCT TTA GCT CAT GTT ACT CAT AAA GAA ATT GTG GAT AAA   1392
Ile Gly Glu Ser Leu Ala His Val Thr His Lys Glu Ile Val Asp Lys
            450                 455                 460

CAA TTG GAG CAT TTC AAG AAA GCT GAT CCC AAA TAC GCT GAG GGA GTT   1440
Gln Leu Glu His Phe Lys Lys Ala Asp Pro Lys Tyr Ala Glu Gly Val
465                 470                 475

AAA AAA GCT CTT GAA AAA CAC CAA AAA ATG ATG AAA GAC ATG CAT GGA   1488
Lys Lys Ala Leu Glu Lys His Gln Lys Met Met Lys Asp Met His Gly
480                 485                 490                 495

AAA GAC ATG CAT CAC ATG AAA AAG AAA AAG TAACCCTTTT CTTTAAGCGT TCT 1541
Lys Asp Met His His Met Lys Lys Lys Lys
            500                 505

TATTTTTTAG GAATGCTTTG TCTTTCAAAA TTTAGGTTTT TGGATACTTG TCAACCCTTT 1601

AGGGTTGGTG GTGTGTCCTA CTTTTTTCAT TCATGCAACG AATTTAAAAA TTACAATAAA 1661

GAGTTATAGT TATGAAACGA AGGGATTTTA TTAAAACGAC TGCTTTAGGC GCTACAGGTG 1721

CTGTTTTAGG AGCACAGATT TTGCAGGCAG AAGAAAGCAA AGGGAGTGTT GCAAAATATA 1781

AAATAGAAGC TCAATACAGC ATTGATTTT                                  1810
```

(2) INFORMATION FOR SEQ ID NO:4:

(i) SEQUENCE CHARACTERISTICS:
        (A) LENGTH: 505 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:4:

```
Met Val Asn Lys Asp Val Lys Gln Thr Thr Ala Phe Gly Ala Pro Val
 1               5                  10                  15
Trp Asp Asp Asn Asn Val Ile Thr Ala Gly Pro Arg Gly Pro Val Leu
                20                  25                  30
Leu Gln Ser Thr Trp Phe Leu Glu Lys Leu Ala Ala Phe Asp Arg Glu
             35                  40                  45
Arg Ile Pro Glu Arg Val Val His Ala Lys Gly Ser Gly Ala Tyr Gly
         50                  55                  60
Thr Phe Thr Val Thr Lys Asp Ile Thr Lys Tyr Thr Lys Ala Lys Ile
 65                  70                  75                  80
Phe Ser Lys Val Gly Lys Lys Thr Glu Cys Phe Phe Arg Phe Ser Thr
                 85                  90                  95
Val Ala Gly Glu Arg Gly Ser Ala Asp Ala Val Arg Asp Pro Arg Gly
            100                 105                 110
Phe Ala Met Lys Tyr Tyr Thr Glu Glu Gly Asn Trp Asp Leu Val Gly
        115                 120                 125
Asn Asn Thr Pro Val Phe Phe Ile Arg Asp Ala Ile Lys Phe Pro Asp
        130                 135                 140
Phe Ile His Thr Gln Lys Arg Asp Pro Gln Thr Asn Leu Pro Asn His
145                 150                 155                 160
Asp Met Val Trp Asp Phe Trp Ser Asn Val Pro Glu Ser Leu Tyr Gln
                165                 170                 175
Val Thr Trp Val Met Ser Asp Arg Gly Ile Pro Lys Ser Phe Arg His
            180                 185                 190
Met Asp Gly Phe Gly Ser His Thr Phe Ser Leu Ile Asn Ala Lys Gly
        195                 200                 205
Glu Arg Phe Trp Val Lys Phe His Phe His Thr Met Gln Gly Val Lys
        210                 215                 220
His Leu Thr Asn Glu Glu Ala Ala Glu Val Arg Lys Tyr Asp Pro Asp
225                 230                 235                 240
Ser Asn Gln Arg Asp Leu Phe Asn Ala Ile Ala Arg Gly Asp Phe Pro
                245                 250                 255
Lys Trp Lys Leu Ser Val Gln Val Met Pro Glu Glu Asp Ala Lys Lys
            260                 265                 270
Tyr Arg Phe His Pro Phe Asp Val Thr Lys Ile Trp Tyr Leu Gln Asp
        275                 280                 285
Tyr Pro Leu Met Glu Val Gly Ile Val Glu Leu Asn Lys Asn Pro Glu
        290                 295                 300
Asn Tyr Phe Ala Glu Val Glu Gln Ala Ala Phe Ser Pro Ala Asn Val
305                 310                 315                 320
Val Pro Gly Ile Gly Tyr Ser Pro Arg Met Leu Gln Gly Arg Leu
                325                 330                 335
Phe Ser Tyr Gly Asp Thr His Arg Tyr Arg Leu Gly Val Asn Tyr Pro
        340                 345                 350
Gln Ile Pro Val Asn Lys Pro Arg Cys Pro Phe His Ser Ser Ser Arg
        355                 360                 365
Asp Gly Tyr Met Gln Asn Gly Tyr Tyr Gly Ser Leu Gln Asn Tyr Thr
        370                 375                 380
Pro Ser Ser Leu Pro Gly Tyr Lys Glu Asp Lys Ser Ala Arg Asp Pro
385                 390                 395                 400
Lys Phe Asn Leu Ala His Ile Glu Lys Glu Phe Glu Val Trp Asn Trp
```

-continued

```
                405                 410                 415
Asp Tyr Arg Ala Asp Asp Ser Asp Tyr Tyr Thr Gln Pro Gly Asp Tyr
            420                 425                 430

Tyr Arg Ser Leu Pro Ala Asp Glu Lys Glu Arg Leu His Asp Thr Ile
            435                 440                 445

Arg Glu Ser Leu Ala His Val Thr His Lys Glu Ile Val Asp Lys Gln
            450                 455                 460

Leu Glu His Phe Lys Lys Ala Asp Pro Lys Tyr Ala Glu Gly Val Lys
465                 470                 475                 480

Lys Ala Leu Glu Lys His Gln Lys Met Met Lys Asp Met His Gly Lys
                485                 490                 495

Asp Met His His Thr Lys Lys Lys
                500                 505
```

(2) INFORMATION FOR SEQ ID NO:5:

(i) SEQUENCE CHARACTERISTICS:
        (A) LENGTH: 505 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:5:

```
Met Val Asn Lys Asp Val Lys Gln Thr Thr Ala Phe Gly Ala Pro Val
1               5                   10                  15

Trp Asp Asp Asn Val Ile Thr Ala Gly Pro Arg Gly Pro Val Leu
                20                  25                  30

Leu Gln Ser Thr Trp Phe Leu Glu Lys Leu Ala Ala Phe Asp Arg Glu
            35                  40                  45

Arg Ile Pro Glu Arg Val Val His Ala Lys Gly Ser Gly Ala Tyr Gly
            50                  55                  60

Thr Phe Thr Val Thr Lys Asp Ile Thr Lys Tyr Thr Lys Ala Lys Ile
65                  70                  75                  80

Phe Ser Lys Val Gly Lys Lys Thr Glu Cys Phe Phe Arg Phe Ser Thr
                85                  90                  95

Val Ala Gly Glu Arg Gly Ser Ala Asp Ala Val Arg Asp Pro Arg Gly
                100                 105                 110

Phe Ala Met Lys Tyr Tyr Thr Glu Glu Gly Asn Trp Asp Leu Val Gly
            115                 120                 125

Asn Asn Thr Pro Val Phe Phe Ile Arg Asp Ala Ile Lys Phe Pro Asp
        130                 135                 140

Phe Ile His Thr Gln Lys Arg Asp Pro Gln Thr Asn Leu Pro Asn His
145                 150                 155                 160

Asp Met Val Trp Asp Phe Trp Ser Asn Val Pro Glu Ser Leu Tyr Gln
                165                 170                 175

Val Thr Trp Val Met Ser Asp Arg Gly Ile Pro Lys Ser Phe Arg His
                180                 185                 190

Met Asp Gly Phe Gly Ser His Thr Phe Ser Leu Ile Asn Ala Lys Gly
            195                 200                 205

Glu Arg Phe Trp Val Lys Phe His Phe His Thr Met Gln Gly Val Lys
        210                 215                 220

His Leu Thr Asn Glu Glu Ala Ala Glu Val Arg Lys Tyr Asp Pro Asp
225                 230                 235                 240
```

```
Ser Asn Gln Arg Asp Leu Phe Asn Ala Ile Ala Arg Gly Asp Phe Pro
            245                 250                 255

Lys Trp Lys Leu Ser Val Gln Val Met Pro Glu Glu Asp Ala Lys Lys
            260                 265                 270

Tyr Arg Phe His Pro Phe Asp Val Thr Lys Ile Trp Tyr Leu Gln Asp
            275                 280                 285

Tyr Pro Leu Met Glu Val Gly Ile Val Glu Leu Asn Lys Asn Pro Glu
            290                 295                 300

Asn Tyr Phe Ala Glu Val Glu Gln Ala Ala Phe Ser Pro Ala Asn Val
305                 310                 315                 320

Val Pro Gly Ile Gly Tyr Ser Pro Asp Arg Met Leu Gln Gly Arg Leu
                325                 330                 335

Phe Ser Tyr Gly Asp Thr His Cys Tyr Arg Leu Gly Val Asn Tyr Pro
                340                 345                 350

Gln Ile Pro Val Asn Lys Pro Arg Cys Pro Phe His Ser Ser Ser Arg
                355                 360                 365

Asp Gly Tyr Met Gln Asn Gly Tyr Tyr Gly Ser Leu Gln Asn Tyr Thr
                370                 375                 380

Pro Ser Ser Leu Pro Gly Tyr Lys Glu Asp Lys Ser Ala Arg Asp Pro
385                 390                 395                 400

Lys Phe Asn Leu Ala His Ile Glu Lys Glu Phe Glu Val Trp Asn Trp
                405                 410                 415

Asp Tyr Arg Ala Asp Asp Ser Asp Tyr Tyr Thr Gln Pro Gly Asp Tyr
                420                 425                 430

Tyr Arg Ser Leu Pro Ala Asp Glu Lys Glu Arg Leu His Asp Thr Ile
                435                 440                 445

Gly Glu Ser Leu Ala His Val Thr His Lys Glu Ile Val Asp Lys Gln
                450                 455                 460

Leu Glu His Phe Lys Lys Ala Asp Pro Lys Tyr Ala Glu Gly Val Lys
465                 470                 475                 480

Lys Ala Leu Glu Lys His Gln Lys Met Met Lys Asp Met His Gly Lys
                485                 490                 495

Asp Met His His Thr Lys Lys Lys Lys
                500                 505

(2) INFORMATION FOR SEQ ID NO:6:

(i) SEQUENCE CHARACTERISTICS:
        (A) LENGTH: 505 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:6:

Met Val Asn Lys Asp Val Lys Gln Thr Thr Ala Phe Gly Ala Pro Val
1               5                   10                  15

Trp Asp Asp Asn Asn Val Ile Thr Ala Gly Pro Arg Gly Pro Val Leu
                20                  25                  30

Leu Gln Ser Thr Trp Phe Leu Glu Lys Leu Ala Ala Phe Asp Arg Glu
                35                  40                  45

Arg Ile Pro Glu Arg Val Val His Ala Lys Gly Ser Gly Ala Tyr Gly
            50                  55                  60
```

```
Thr Phe Thr Val Thr Lys Asp Ile Thr Lys Tyr Thr Lys Ala Lys Ile
65                  70                  75                  80

Phe Ser Lys Val Gly Lys Lys Thr Glu Cys Phe Phe Arg Phe Ser Thr
                85                  90                  95

Val Ala Gly Glu Arg Gly Ser Ala Asp Ala Val Arg Asp Pro Arg Gly
            100                 105                 110

Phe Ala Met Lys Tyr Tyr Thr Glu Glu Gly Asn Trp Asp Leu Val Gly
        115                 120                 125

Asn Asp Thr Pro Val Phe Phe Ile Arg Asp Ala Ile Lys Phe Pro Asp
    130                 135                 140

Phe Ile His Thr Gln Lys Arg Asp Pro Gln Thr Asn Leu Pro Asn Pro
145                 150                 155                 160

Asp Met Val Trp Asp Phe Trp Ser Asn Val Pro Glu Ser Leu Tyr Gln
                165                 170                 175

Val Thr Trp Val Met Ser Asp Arg Gly Ile Pro Lys Ser Phe Arg His
            180                 185                 190

Met Asp Gly Phe Gly Ser His Thr Phe Ser Leu Ile Asn Ala Lys Gly
        195                 200                 205

Glu Arg Phe Trp Val Lys Phe His Phe Leu Thr Met Gln Gly Val Lys
    210                 215                 220

His Leu Thr Asn Glu Glu Ala Ala Glu Ile Arg Lys His Asp Pro Asp
225                 230                 235                 240

Ser Asn Gln Arg Asp Leu Phe Asp Ala Ile Ala Arg Gly Asp Phe Pro
                245                 250                 255

Lys Trp Lys Leu Ser Ile Gln Val Met Pro Glu Glu Asp Ala Lys Lys
            260                 265                 270

Tyr Arg Phe His Pro Phe Asp Val Thr Lys Ile Trp Cys Leu Lys Asp
        275                 280                 285

Tyr Pro Leu Thr Glu Val Gly Ile Val Glu Leu Asn Lys Asn Pro Glu
    290                 295                 300

Asn Tyr Phe Ala Glu Val Glu Gln Ala Ala Phe Thr Pro Ala Asn Val
305                 310                 315                 320

Val Pro Gly Ile Gly Tyr Ser Pro Asp Arg Met Leu Gln Gly Arg Leu
                325                 330                 335

Phe Ser Tyr Gly Asp Thr His Arg Tyr Arg Leu Gly Val Asn Tyr Pro
            340                 345                 350

Gln Ile Pro Val Asn Arg Pro Arg Cys Pro Phe His Ser Ser Ser Arg
        355                 360                 365

Asp Gly Tyr Met Gln Asn Gly Tyr Tyr Gly Ser Leu Gln Asn Tyr Thr
    370                 375                 380

Pro Ser Ser Leu Pro Gly Tyr Lys Glu Asp Lys Ser Thr Arg Asp Pro
385                 390                 395                 400

Lys Phe Asn Leu Ala His Ile Glu Lys Glu Phe Glu Val Trp Asn Trp
                405                 410                 415

Asp Tyr Arg Ala Asp Asp Ser Asp Tyr Tyr Thr Gln Pro Gly Asp Tyr
            420                 425                 430

Tyr Arg Ser Leu Pro Ala Asp Glu Lys Glu Arg Leu His Asp Thr Ile
        435                 440                 445

Gly Glu Ser Leu Ala His Val Thr His Lys Glu Ile Val Asp Lys Gln
    450                 455                 460

Leu Glu His Phe Lys Lys Ala Asp Pro Lys Tyr Ala Glu Gly Val Lys
465                 470                 475                 480

Lys Ala Leu Glu Lys His Gln Lys Met Met Lys Asp Met His Gly Lys
```

-continued

```
                485                 490                 495
Asp Met His His Met Lys Lys Lys Lys
                500                 505
```